(12) United States Patent
Önyüksel et al.

(10) Patent No.: US 6,217,886 B1
(45) Date of Patent: Apr. 17, 2001

(54) MATERIALS AND METHODS FOR MAKING IMPROVED MICELLE COMPOSITIONS

(75) Inventors: Hayat Önyüksel, Western Springs; Israel Rubinstein, Highland Park, both of IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/239,069

(22) Filed: Jan. 27, 1999

Related U.S. Application Data

(63) Continuation-in-part of application No. PCT/US98/14316, filed on Jul. 9, 1998.
(60) Provisional application No. 60/052,078, filed on Jul. 14, 1997.

(51) Int. Cl.$^7$ ................................ A61K 9/10; A61K 9/127
(52) U.S. Cl. .................... 424/401; 424/450; 424/1.21; 424/9.321; 424/9.51; 514/2; 514/21; 514/937; 264/4.1; 264/4.3; 264/4.6
(58) Field of Search .................. 424/450, 1.21, 424/9.321, 9.51, 417, 96.3, 401; 514/2, 21, 937–943; 264/4.1, 4.3, 4.6

(56) References Cited

U.S. PATENT DOCUMENTS

| | | | |
|---|---|---|---|
| 4,529,561 | 7/1985 | Hunt et al. | 264/4.3 |
| 4,920,016 | 4/1990 | Allen et al. | 424/450 |
| 5,013,556 | 5/1991 | Woodle et al. | 424/450 |
| 5,225,212 | 7/1993 | Martin et al. | 424/450 |
| 5,230,882 | 7/1993 | Unger | 424/9 |
| 5,374,548 | 12/1994 | Caras | 424/450 |
| 5,484,894 | 1/1996 | Woiszwillo | 530/410 |
| 5,514,670 | 5/1996 | Friedman et al. | 514/2 |
| 5,534,241 | 7/1996 | Torchilin et al. | 424/9.321 |
| 5,542,935 | 8/1996 | Unger et al. | 604/190 |
| 5,543,390 | 8/1996 | Yatvin et al. | 514/2 |
| 5,545,569 | 8/1996 | Grainger et al. | 436/518 |
| 5,552,156 | 9/1996 | Burke | 424/450 |
| 5,567,410 | 10/1996 | Torchilin et al. | 424/9.4 |
| 5,573,934 | 11/1996 | Hubbell et al. | 435/177 |
| 5,578,709 | 11/1996 | Woiszwillo | 530/410 |
| 5,580,575 | 12/1996 | Unger et al. | 424/450 |
| 5,580,853 | 12/1996 | Sytkowski | 514/8 |
| 5,585,112 | 12/1996 | Unger et al. | 424/450 |
| 5,587,149 | 12/1996 | Punto et al. | 424/59 |
| 5,589,453 | 12/1996 | Greve et al. | 514/8 |
| 5,595,722 | 1/1997 | Grainger et al. | 424/9.2 |
| 5,612,027 | 3/1997 | Galin et al. | 424/78.04 |
| 5,633,226 | 5/1997 | Owen et al. | 514/2 |
| 5,635,187 | 6/1997 | Bathurst et al. | 424/195.1 |
| 5,736,156 | * 4/1998 | Burke | 424/450 |

FOREIGN PATENT DOCUMENTS

| | | |
|---|---|---|
| 0082311 | 5/1982 | (JP) . |
| WO 93/20802 | 10/1993 | (WO) . |
| WO 95/27496 | 10/1995 | (WO) . |
| WO 97/35560 | 10/1997 | (WO) . |
| WO 97/35561 | 10/1997 | (WO) . |

OTHER PUBLICATIONS

Trubetskoy in Proceed. Intern. Symp. Control Rel. Bioact. Mat. 22, p 452–453, 1995.*

Alessandrini, F. et al., "Vasoactive Intestinal Peptide Enhances Lung Preservation," *Transplantation*, 56(4):964–973 (Oct., 1993).

(List continued on next page.)

*Primary Examiner*—Gollamudi S. Kishore
(74) *Attorney, Agent, or Firm*—Marshall, O'Toole, Gerstein, Murray & Borun

(57) ABSTRACT

Provided are methods for preparing improved biologically active micelle and crystalline products comprising a biologically active amphipathic compound in association with a micelle or crystalline product. Methods for producing the micelle or crystalline products as well as methods of using the micelle or crystalline products in therapeutic, diagnostic, and cosmetic, applications are also provided.

34 Claims, 8 Drawing Sheets

OTHER PUBLICATIONS

Alexandridis, P. et al., "Temperature Effects of Structural Properties of Pluronic P104 and F108 PEO–PPO–PEO Block Copolymer Solutions," *Langmuir*, 11:1468–1476 (1995).

Alkan–Onyuksel, H. et al., "A Mixed Micellar Formulation Suitable for the Parenteral Administration of Taxol," *Pharmaceutical Research*, 11(2):206–212 (1994).

Alkan–Onyuksel, H. et al., "Development of Inherently Echogenic Liposomes as an Ultrasonic Contrast Agent," *Journal of Pharmaceutical Sciences*, 85(5):486–490 (May, 1996).

Allen, T.M. et al., "Large Unilamellar Liposomes with Low Uptake into the Reticuloendothelial System," *Federation European Biochemical Societies*, 223(1):42–46 (Oct., 1987).

Allen, T.M. et al., "Liposomes containing synthetic lipid derivatives of poly(ethylene glycol) show prolonged circulation half–lives in vivo," *Biochimica et Biophysica Acta*, 1066:29–36 (1991).

Almgren, M. et al., "Self–aggregation and phase behavior of poly(ethylene oxide)–poly(propylene oxide)–poly(ehtylene oxide) block copolymers in aqueous solution," *Colloid Polym Sci.*, 273:2–15 (1995).

Artwohl, J.F. et al., "Initial Characterization of Hamsters with Spontaneous Hypertension," *FASEB J.*, 10:A628 (1996).

Avidor, R. et al., "VIP–mRNA is increased in hypertensive rats," *Brain Research*, 503:304–307 (1989).

Bangham, A.D. et al., "Diffusion of Univalent Ions across the Lamellae of Swollen Phospholipids," *J. Mol. Biol.*, 13:238–252 (1965).

Beaumier, P.L. et al., "Effect of Liposome Dose on the Elimination of Small Unilamellar Sphingomyelin/Cholesterol Vesicles from the Circulation," *Research Communications in Chemical Pathology and Pharmacology*, 39(2):277–289 (Feb., 1983).

Beaumier, P.L. et al., "Effects of Liposome Size on the Degradation of Bovine Brain Sphingomyelin/Cholesterol Liposomes in the Mouse Liver," *Biochimica et Biophysica Acta*, 731:23–30 (1983).

Bedu–Addo, F.K. et al., "Interaction of Polyethyleneglycol–Phospholipid Conjugates with Cholesterol–Phosphatidylcholine Mixtures: Sterically Stabilized Liposome Formulations," *Pharmaceutical Research*, 13(5):718–724 (1996).

Berisha, H. et al., "Vasoactive intestinal peptide prevents lung injury due to xanthine oxidase," *Am. J. Physiol.*, 259:L151–L155 (1990).

Bodanszky, M. et al., "A Preferred Conformation in the Vasoactive Intestinal Peptide (VIP). Molecular Architecture of Gastrointestinal Hormones," *Bioorganic Chemistry*, 3:133–140 (1974).

Bolin, D.R. et al., "Design and Development of a Vasoactive Intestinal Peptide Analog as a Novel Therapeutic for Bronchial Asthma," *Biopolymers*, (*Peptide Science*) 37:57–66 (1995).

Carey, M.C. et al., "Micelle Formation by Bile Salts," *Arch Inter. Med.*, 130:506–527 (Oct., 1972).

Chiba, K. et al., "Interaction Between Lipids and Bovine Brain Calmodulin: Lysophosphatidylcholine–Induced Conformation Change," *Life Science*, 47:953–960 (1990).

Damrongchai, N. et al., "Calcium Responsive Two–Dimensional Molecular Assembling of Lipid–Conjugated Calmodulin," *Bioconjugate Chem.*, 6:264–268 (1995).

DeGrado, W.F. et al., "Induction of Peptide Conformation at Apolar/Water Interfaces. 1. A Study with Model Peptides of Defined Hydrophobic Periodicity," *J. Am. Chem. Soc.*, 107:7684–7689 (1985).

Demos, S.M. et al., "In Vitro Targeting of Antibody–Conjugated Echogenic Liposomes for Site–Specific Ultrasonic Image Enhancement," *Journal of Pharmaceutical Sciences*, 86(2):167–171 (Feb., 1997).

Fournier, A. et al., "Synthesis, Conformational Studies and Biological Activities of VIP and Related Fragments," *Peptides* 5:169–177 (1984).

Frase, L.L. et al., "Cardiovascular Effects of Vasoactive Intestinal Peptide in Healthy Subjects," *Am. J. Cardio.*, 60:1356–1361 (1987).

Fry, D.C. et al., "Solution Structure of an Analogue of Vasoactive Intestinal Peptide As Determined by Two–Dimensional NMR and Circular Dichroism Spectroscopies and Constrained Molecular Dynamics," *Biochemistry*, 28:2399–2409 (1989).

Gabizon, A. et al., "Liposome Formulations with Prolonged Circulation Time in Blood and Enhanced Uptake by Tumors," *Proc. Natl. Acad. Sci.* (*USA*), 85:6949–6953 (Sep., 1988).

Gao, X. et al., "Loop diuretics attenuate bradykinin–induced increase in clearance of macromolecules in the oral mucosa," *J. Appl. Physiol.*, 80(3):818–823 (1996).

Gao, X. et al., "Vasoactive Intestinal Peptide Encapsulated in Liposomes: Effects on Systemic Arterial Blood Pressure," *Life Sciences*, 54(15): PL247–PL252 (1994).

Gozes, I. et al., "VIP: Molecular Biology and Neurobiological Function," *Molecular Neurobiology*, 3:201–236 (1989).

Gozes, I. et al., "Stearyl–Norleucine–Vasoactive Intestinal Peptide (VIP): A Novel VIP Analog for Noninvasive Impotence Treatment," *Endorinology*, 134(5):2121–2125 (1994).

Gozes, I. et al., "Superactive Lipophilic Peptides Discriminate Multiple Vasoactive Intestinal Peptide Receptors," *J. Pharmacology Experimental Therapeutics*, 273(1):161–167 (1995).

Gregoriadias, G. et al., "Fate of Protein–Containing Liposomes Injected into Rats: An Approach to the Treatment of Storage Diseases," *Eur. J. Biochem.* 24:485–491 (1972).

Gregoriadis, G. et al., "Liposomes in Drug Delivery: Clinical, Diagnostic and Ophthalmic Potential," *Drugs*, 45(1):15–28 (1993).

Haghjoo, K. et al., "Solution Structure of Vasoactive Intestinal Polypeptide (11–28)–$NH_2$, a Fragment with Analgesic Properties," *Peptide Research*, 9(6):327–331 (1996).

Hamed, M.M. et al., "Behavior of Amphipathic Helices on Analysis via Matrix Methods, with Application to Glucagon, Secretin, and Vasoactive Intestinal Peptide," *Biopolymers*, 22:1003–1021 (1983).

Hirata, Y. et al., "Functional Receptors For Vasoactive Intestinal Peptide In Cultured Vascular Smooth Muscle Cells From Rat Aorta," *Biochemical Biophysical Research Communications*, 132(3):1079–1087 (Nov., 1985).

Hjelm, R.P. Jr. et al., "Organization of Phosphatidylcholine and Bile Salt in Rodlike Mixed Micelles," *J. Phys. Chem.*, 96(21):8653–8661 (1992).

Hökfelt, T., "Neuropeptide in Perspective: The Last Ten Years," *Neuron*, 7:867–879 (1991).

Houbre, D. et al., "The Interactions of the Brain–specific Calmodulin–binding Protein Kinase C Substrate, Neuromodulin (GAP 43), with Membrane Phospholipids," *Journal Biological Chemistry*, 266(11):7121–7131 (Apr., 1991).

Hristova, K. et al., "Effect of Bilayer Composition on the Phase Behavior of Liposomal Suspensions Containing Poly(ethylene glycol)–Lipids," *Macromolecules*, 28(23):7793–7799 (1995).

Hristova, K. et al., "Phase Behavior of a Lipid/Polymer–Lipid Mixture in Aqueous Medium," *Macromolecules*, 28:991–1002 (1995).

Hwang, K.J., "Liposome Pharmacokinetics," in *Liposomes from Biophysics to Therapeutics*, Ostro, M.J. (Ed.), Marcel Dekker, Inc., New York, pp. 109–156 (1987).

Kaiser, E.T. et al., "Peptides with Affinity for Membranes," *Ann. Rev. Biophys. Biophysical Chem.*, 16:561–581 (1987).

Kates, M., in *Laboratory Techniques in Biochemistry and Molecular Biology: Techniques in Lipidology Isolation, Analysis and Identification of Lipids*, Work, T.S. et al., (Eds.) North–Holland/American Elsevier, New York, New York, USA, pp. 354–356 (1972).

Kedar, E. et al., "Delivery of Cytokines by Liposomes. I. Preparation and Characterization of Interleukin–2 Encapsulated in Long–Circulating Sterically Stabilized Liposomes," *Journal of Immunotherapy*, 16:47–59 (1994).

Kenworthy, A.K. et al., "Structure and Phase Behavior of Lipid Suspensions Containing Phospholipids with Covalently Attached Poly(ethylene glycol)," *Biophysical Journal*, 68:1903–1920 (May, 1995).

Kirby, C. et al., "Dehydration–Rehydration Vesicles: A Simple Method for High Yield Drug Entrapment in Liposomes," *Biotechnology*, pp. 979–984 (Nov. 1984).

Kirby, C. et al., "Effect of the Cholesterol Content of Small Unilamellar Liposomes on their Stability in vivo and in vitro," *Biochem. J.*, 186:591–598 (1980).

Klibanov, A.L. et al., "Activity of amphipathic poly(ethylene glycol) 5000 tp prolong the circulation time of liposomes depends on the liposome size and is unfavorable for immunoliposome binding to target," *Biochimica Biophysica Acta*, 1062:142–148 (1991).

Klibanov, A.L. et al., "Amphipathic polyethyleneglycols effectively prolong the circulation time of liposomes," *FEBS Lett.*, 268(1):235–237 (Jul., 1990).

Krejs, G.J., "Effect of Vasoactive Intestinal Peptide in Man," *Am. N.Y. Acad. Sci.*, 527:501–507 (1988).

Lasic, D. et al., *Stealth Liposomes*, Lasic, D. et al., (Eds.), CRC Press, Inc., Boca Raton, FL, pp. 1–289 (1995).

Li, P. et al., "Comparison of Bile Salt/Phosphotidylcholine Mixed Micelles to Poly (Ethylene Glycol) 2000 Conjugated Distearoyl–Phophoethananolamine Phosphotidylcholine Mixed Micelles," *Parental and Mucosal Drug Delivery*, p. S–582–S–583 (Nov., 1998) (Abstract).

Litzinger, D.C. et al., "Effect of Liposome Size on the Circulation Time and Intraorgan Distribution of Amphipathic Poly(ethylene glycol)–Containing Liposomes," *Biochimica et Biophysica Acta*, 1190:99–107 (1994).

Liu, D. et al., "Role of liposome size and RES blockade in controlling biodistribution and tumor uptake $GM_1$–containing liposomes," *Biochimica et Biophysica Acta*, 1104:95–101 (1992).

Lutz, E.M. et al., "The $VIP_2$ receptor: molecular characterisation of a cDNA encoding a novel receptor for vasoactive intestinal peptide," *FEBS Lett*, 334(1):3–8 (Nov., 1993).

MacDonald, R.C. et al., "Small–Volume Extrusion Apparatus for Preparation of Large, Unilamellar Vesicles," *Biochimica et Biophysica Acta*, 1061:297–303 (1991).

Malhotra, R.K. et al., "Vasoactive Intestinal Polypeptide and Muscarine Mobilize Intracellular $Ca^{2+}$ through Breakdown of Phosphoinositides to Induce Catecholamine Secretion," *Journal of Biological Chemistry*, 263(5):2123–2126 (1988).

Maruyama, K. et al., "Effect of Molecular Weight in Amphopathic Polyehtyleneglycol on Prolonging the Circulation Time of Large Unilamellar Liposomes," *Chem. Pharm. Bull.*, 39(6):1620–1622 (1991).

Mayhan, W.G. et al., "Acetylcholine Induces Vasoconstriction in the Microcirculation of Cardiomyopathetic Hamsters: Reversal by L–Arginine," *Biochemical and Biophysical Research Communications*, 184(3):1372–1377 (May, 1992).

Mayhan, W.G. et al., "The Effect of Altering the External Calcium Concentration and a Calcium Channel Blocker, Verapamil, on Microvascular Leaky Sites and Dextran Clearance in the Hamster Cheek Pouch," *Microvascular Research*, 28:159–179 (1984).

Morice, A. et al., "Vasoactive Intestinal Peptide Causes Bronchodilatation and Protects Against Histamine–Induced Bronchoconstriction in Asthmatic Subjects," *Lancet*, 262(8361):1225–1227 (Nov., 1983).

Muller, J. et al., "VIP as a Cell–Growth and Differentiation Neuromodulator Role in Neurodevelopment," *Molecular Neurobiology*, 10:115–134 (1995).

Muranushi, N. et al., "Effect Of Fatty Acids And Monoglycerides On Permeability Of Lipid Bilayer," *Chemistry and Physics of Lipids*, 28:269–279 (1981).

Musso, G.F. et al., "Development of Helix–Based Vasoactive Intestinal Peptide Analogues: Identification of Residues Required for Receptor Interaction," *Biochemistry*, 27:8174–8181 (1988).

Nivaggioli, T. et al., "Fluorescence Probe Studies of Pluronic Copolymer Solutions as a Function of Temperature," *Langmuir*, 11(3):730–737 (1995).

Noda, Y. et al., "Partitioning of Vasoactive Intestinal Polypeptide into Lipid Bilayers," *Biochimica et Biophysica Acta*, 1191:324–330 (1994).

Nucci, M.L. et al., "The Therapeutic Value of Poly(ethylene glycol)–Modified Proteins," *Advanced Drug Delivery Reviews*, 6:133–151 (1991).

Ollerenshaw, S. et al., "Absence of Immunoreactive Vasoactive Intestinal Polypeptide in Tissue from the Lungs of Patients with Asthma," *New England Journal of Medicine*, 320:1244–1248 (May, 1989).

Omary, M.B. et al., "Identification of Nuclear Receptors for VIP on a Human Colonic Adenocarcinoma Cell Line," *Science*, 238:1578–1581 (1987).

Patel, M. et al., "Simplified Preparation of Vasoactive Intestinal Peptide in Sterically Stabilized Liposomes," *Proceedings of International Symposium on Controlled Release Bioactive Materials*, 24:913–914 (1997).

Patel, M., "Study of Interactions Between Vasoactive Intestinal Peptide and Phospholipid Vesicles and Micelles," Masters Thesis, University of Illinois at Chicago, Chicago, Illinois (1997).

Paul, S. et al., "Regulatory Aspects of the Vasoactive Intestinal Peptide Receptor in Lung," *Ann. N.Y. Acad. Sci.*, 527:282–295 (1988).

Paul, S., "Vasoactive Intestinal Peptide: Its Interactions with Calmodulin and Catalytic Antibodies," *Neurochem. Int.*, 23(3):197–214 (1993).

Raud, J., "Intravital Microscopic Studies on Acute Mast Cell–Dependent Inflammation," *Acta Physiologica Scandinavica Supplementum* 578:1–58 (1989).

Robinson, R.M. et al., "Lipid–Induced Conformational Changes in Glucagon, Secretin, and Vasoactive Intestinal Peptide," *Biopolymers*, 21(6):1217–1228 (Jun. 1982).

Rorstad, O.P. et al., "Selectivity for Binding of Peptide Analogs to Vascular Receptors for Vasoactive Intestinal Peptide," *Molecular Pharmacology*, 37:971–977 (1990).

Rubinstein, I. et al., "Tissue Angiotensin I–Converting Enzyme Activity in Spontaneously Hypertensive Hamsters," *Biochemical and Biophysical Research Communications*, 183(3):1117–1123 (Mar., 1992).

Rubinstein, I. et al., "Cigarette Smoke Extract Attenuates Endothelium–Dependent Arteriolar Dilatation In Vivo," *Am. J. Physiol.*, 261 (*Heart Circ. Physiol.* 30):H1913–H1918 (1991).

Rubinstein, I., "L–Arginine Dilates Cheek Pouch Arterioles in Hamsters with Hereditary Cardiomyopathy but not in Controls," *J. Lab. Clin. Med.*, 125:313–318 (1995).

Said, S.I., "Vasoactive Intestinal Peptide (VIP) and Related Peptides as Anti–Asthma and Anti–Inflammatory Agents," *Biomedical Research*, 13(Supplement 2):257–262 (1992).

Said, S.I., "Vasoactive Intestinal Polypeptide (VIP): Current Status," *Peptides*, 5:143–150 (1984).

Said, S.I., "Vasoactive Intestinal Polypeptide: Biological Role in health and Disease," *Trends Endocrinology Metab.*, 2(3):107–112 (1991).

Saletu, B. et al., "Comparative Bioavailability Studies with a New Mixed–micelles Solution of Diazepam Utilizing Radioreceptor Assay, Psychometry and EEG Brain Mapping," *International Clinical Psychopharmacology*, 3:287–323 (1988).

Sansom, M.S.P., "The Biophysics of Peptide Models of Ion Channels," *Prog. Biophys. Molec. Biol.*, 55:139–235 (1991).

Séjourné et al., "Development of a Bioactive Formulation of Vasoactive Intestinal Peptide in Sterically Stabilized Liposomes," Pharm. Res., 13(Suppl. 9):S–95 (1996).

Séjourné, F. et al., "Mechanisms of vasodilation elicited by VIP in sterically stabilized liposomes in vivo," *American Journal of Physiology*, 273:R287–R292 (1997).

Séjourné, F. et al., "Development of a Novel Bioactive Formulation of Vasoactive Intestinal Peptide in Sterically Stabilized Liposomes," *Pharmaceutical Research*, 14(3):362–365 (1997).

Shiraga, H. et al., "Inhibition of calmodulin–dependent myosin light–chain kinase by growth–hormone–releasing factor and vasoactive intestinal peptide," *Biochem. J.*, 300:901–905 (1994).

Smiley, J.D., "Southwestern Internal Medicine Conference: The Many Faces of Scleroderma," *American Journal Medical Sciences*, 304:319–333 (1992).

Soloviev, A.I. et al., "Phospholipid Vesicles (Liposomes) Restore Endothelium–Dependent Cholinergic Relaxation in Thoracic Aorta from Spontaneously Hypertensive Rats," *J. Hypertension*, 11:623–627 (1993).

Sreedharan, S.P. et al., "Human Vasoactive Intestinal Peptide Receptors Expressed By Stable Transfectants Couple To Two Distinct Signaling Pathways," *Biochemical Biophysical Research Communications*, 203(1):141–148 (Aug., 1994).

Stallwood, D. et al., "Identity of a Membrane–bound Vasoactive Intestinal Peptide–binding Protein with Calmodulin," *Journal of Biological Chemistry*, 267(27):19617–19621 (Sep., 1992).

Suzuki, H. et al., "Encapsulation of VIP into Liposomes Restores Vasorelaxation in Hypertension in Situ," *American Journal of Physiology*, 271(*Heart Circ. Physiol.*, 40):H282–H287 (1996).

Suzuki, H. et al., "Encapsulation of Vasoactive Intestinal Peptide into Liposomes: Effects on Vasodilation in Vivo," *Life Sciences*, 57(15):1451–1457 (1995).

Suzuki, H. et al., "Neutral Endopeptidase Modulates VIP–Induced Vasodilation in Hamster Cheek Pouch Vessels In Situ," *Am. J. Physiol.*, 271(2 pt. 2):R393–397 (Aug., 1996).

Szucs, M. et al., "Lyophilization and Rehydration of Polymer–coated Lipid Vesicles Containing a Lipophilic Chelator in the Presence of Sucrose: Labeling with $^{99m}$Tc and Biodistribution Studies," *Nucl. Med. Biol.*, 22(2):263–268 (1995).

Theriault, Y. et al., "Structural Determination of the Vasoactive Intestinal Peptide by Two–Dimensional H–NMR Spectroscopy," *Biopolymers*, 31:459–464 (1991).

Torchilin, V.P. et al. "Polymers on the Surface of Nanocarriers: Modulation of Carrier Properties and Biodistribution," *Polymer Science*, 36(11):1585–1598 (1994).

Torchilin, V.P., "Polymer–coated long–circulating microparticulate pharmaceuticals," *J. Microencapsulation*, 15(1):1–19 (1988).

Trubetskoy, V. et al., "Micellar Solubilization of Poorly Soluble or Amphiphilic Substances Using Polyoxyethylene–Lipid Conjugates," *Proceedings of International Symposium of Controlled Release Bioactive Materials*, 22:452–453 (1995).

Trubetskoy, V.S. et al., "Stable Polymeric Micelles: Lymphangiographic Contrast Media for Gamma Scintigraphy and Magnetic Resonance Imaging," *Acad. Radiol.*, 3:232–238 (1996).

Trubetskoy, V.S. et al., "Polyethyleneglycol based micelles as carriers of therapeutic and diagnostic agents," *S.T.P. Pharma Sciences*, 6(1):79–86 (1996).

Trubetskoy,, V.S. et al., "Use of polyoxyethylene–lipid conjugates as long–circulating carriers for delivery of therapeutic and diagnostic agents," *Advanced Drug Delivery Reviews*, 16:311–320 (1995).

Watala, C. et al., "Melittin–Induced Alterations in Dynamic Properties of Human Red Blood Cell Membranes," *Chem–Biol. Interactions*, 82:135–149 (1992).

Weissig, V. et al., "A Micellar Delivery System For Dequalinium," *Proceed. Int'l. Symp. Control. Rel. Bioact. Mater.*, 25:415–416 (1998).

Weissig, V. et al., "Accumulation of Protein–Loaded Long–Circulating Micelles and Liposomes in Subcutaneous Lewis Lung Carcinoma in Mice," *Pharmaceutical Research*, 15(10):1552–1556 (1998).

Weissig, V. et al., "Micellar Delivery System For Dequalinium–A Lipophilic Cationic Drug With Anticarcinoma Activity," *Journal of Liposome Research*, 8(3):391–400 (1998).

Woodle, M.C. et al., "Improved Long Circulating (Stealth®) Liposomes Using Synthetic Lipids," *Proceed. Intern. Symp. Control. Rel. Bioact. Mater.*, 17:77–78 (1990).

Woodle, M.C. et al., "Sterically stabilized liposomes," *Biochimica et Biophysica Acta*, 113:171–199 (1992).

Woodle, M.C. et al., "Versatility in Lipid Compositions Showing Prolonged Circulation with Sterically Stabilized Liposomes," *Biochimica et Biophysica Acta*, 1105:193–200 (1992).

Woodle, M.C. et al., "Prolonged Systemic Delivery of Peptide Drugs by Long–Circulating Liposomes: Illustration with Vasopressin in the Brattleboro Rat," *Pharmaceutical Research*, 9(2):260–265 (1992).

Yokoyama, M. et al., "Preparation of adriamycin–conjugated poly(ethylene glycol)–poly (aspartic acid) block copolymer," *Makromal Chem. Rapid Commun.*, 8:431–435 (1987).

Zareie, H.M. et al., "STM images of PDLLA–PEG copolymer micelles," *Colloids and Surfaces A: Physiochemical and Engineering Aspects*, 112:19–24 (1996).

Zia, H. et al., "Breast Cancer Growth Is Inhibited by Vasoactive Intestinal Peptide (VIP) Hybrid, a Synthetic VIP Receptor Antagonist," *Cancer Research*, 56:3486–3489 (Aug., 1996).

Zorn, N.E. et al., "Vasoactive Intestinal Peptide (VIP) Activation of Nuclear Protein Kinase C in Purified Nuclei of Rat Splenocytes," *Biochemical Pharmacology*, 40:2689–2694 (1990).

* cited by examiner

MATERIALS AND METHODS FOR MAKING IMPROVED MICELLE COMPOSITIONS

This application is a continuation-in-part of International Application Number PCT/US98/14316, filed Jul. 9, 1998, which claims the priority benefit under 37 U.S.C. 119(e) of U.S. Provisional Application Ser. No. 60/052,078, filed Jul. 14, 1997.

BACKGROUND OF THE INVENTION

The present invention relates generally to biologically active compounds and more specifically to compounds, peptides, proteins, fragments, analogs, and modulators thereof which are amphipathic, i.e., have both hydrophilic and hydrophobic portions. Specifically, the invention relates to improved methods for the delivery and presentation of amphipathic peptides, proteins, fragments, analogs, and modulators thereof in association with micelles diagnostic, therapeutic, cosmetic and org, an, tissue and cell preservative uses. The invention also provides methods for the delivery of compounds that are insoluble in an aqueous solution. Specifically, the invention provide methods to produce sterically stabilized crystalline products comprised of a crystallized insoluble compound coated with a lipid surface.

Of particular interest to the present invention are the biologically active amphipathic peptides which are members of the family of peptide compounds including, but not limited to, vasoactive intestinal peptide (VIP), growth hormone releasing factor (GRF), peptide histidine isoleucine (PHI), peptide histidine methionine (PHM), pituitary adenylate cyclase activating peptide (PACAP), gastric inhibitory hormone (GIP), hemodermin, the growth hormone releasing hormone (GHRH), sauvagine and urotensin I, secretin, glucagon, galanin, endothelin, calcitonin, $\alpha_1$-proteinase inhibitor, angiotensin II, corticotropin releasing factor, antibacterial peptides and proteins in general, surfactant peptides and proteins, $\alpha$-MSH, adrenolmedullin, ANF, IGF-1, $\alpha$2 amylin, orphanin, and orexin. More specifically, the invention relates to improved therapeutic methods for delivering peptides in the VIP/GRF family of peptides, as well as other amphipathic peptides, to targeted tissues through use of improved micelle compositions comprising a member of the VIP/GRF family of peptides, amphipathic peptides in general, proteins, and biologically active analogues, fragments and modulators thereof.

VIP is a 28-amino acid neuropeptide which is known to display a broad profile of biological actions and to activate multiple signal transducing pathways. See, Said, *Peptides* 5 (Suppl. 1):149–150 (1984) and Paul and Ebadi, *Neurochem. Int.* 23:197–214 (1993). A Schiff-Edmundson projection of VIP as a π-helix reveals segregation of apolar and polar residues onto the opposite faces of the helix and that this amphipathic character is also evident when VIP is modeled as a distorted α-helix, which is reported in Musso, et al., *Biochemistry* 27:8147–8181 (1988). A correlation between the helix-forming tendency of VIP analogues and their biological activity is described in Bodanszky et al., *Bioorgan. Chem.* 3:133–140 (1974). In pure water, the spectral characteristics of VIP are consistent with those of a random coil. However, organic solvents and anionic lipids induce helical-information in the molecule. See, Robinson et al., *Biopolymers* 21:1217–1228 (1983); Hamed, et al., *Biopolymers* 22:1003–1021 (1983); and Bodanszky, et al., *Bioorganic Chem.* 3:133–140 (1974).

Short peptides capable of forming amphipathic helices are known to bind and penetrate lipid bilayers. See, Kaiser and Kezdy, *Ann. Rev. Biophys. Biophysical Chem.* 15:561–581 (1987) and Sansom, *Prog. Biophys. Molec. Biol.* 55:139–235 (1991). Examples include model peptides like (LKKLLKL-), which are disclosed in DeGrado and Lear, *J. Am. Chem. Soc.* 107:7684–7689 (1985), and the 26-residue bee venom peptide, melittin, disclosed in Watata and Gwozdzinski, *Chem-Biol. Interactions* 82:135–149 (1992). Possible mechanisms for the binding include alignment of peptide monomers parallel to the surface of the bilayer mediated by electrostatic interactions between polar amino acids and phospholipid head groups, and insertion of peptide aggregates into the apolar bilayer core, stabilized in part, by the hydrophobic effect. See, Sansom, *Prog. Biophys. Molec. Biol* 55:139–235 (1991).

VIP belongs to a family of homologous peptides, other members of which include peptide histidine isoleucine (PHI), peptide histidine methionine (PBM), growth hormone releasing factor (GRF), pituitary (GIP), hemodermin, the growth hormone releasing hormone (GHRH), sauvagine and utotensin I, secretin and glucagon. Like VIP, the other members of the VIP/GRF family of peptides, and biologically active analogues thereof, can form amphipathic helices capable of binding lipid bilayers. The biological action of members of the VIP/GRF family of peptides are believed to be mediated by protein receptors expressed on the cell surface and intracellular receptors and it has recently been demonstrated that calmodulin is likely to be the intracellular receptor for VIP [Stallwood, et al., *J. Bio. Chem.* 267:19617–19621 (1992); and Stallwood, et al., *FASEB J.* 7:1054 (1993)].

Bodanszky et al., *Bioorgan. Chem.* 3:133–140 (1974) were the first to study the conformation of VIP through optical rotary dispersion and circular dichroism spectrum. They showed structural differences in VIP, depending on the hydrophobicity of the solvent in which VIP was dissolved. The VIP-in-water spectrum revealed a mostly random coil structure (about 80%). However, addition of organic solvents, such as trifluoroethanol (TFE) or methanol, even at low concentration induced a pronounced shift to a helical structure. The authors suggested that these effects of the organic solvents on the structure of the peptide would coincide with receptor conditions, and therefore, the helical conformation of VIP would correspond to an "active architecture" required for its biological activity. These early studies were in agreement with the findings of Robinson et al., *Biopolymers* 21:1217–1228 (1982), who analyzed the conformation of VIP, and two of its family members, secretin and glucagon, in water, anionic detergents, and anionic lipids (PA and phosphatidylglycerol (PG)). They showed an increase in the helix formation probability by arginyl, histidyl, and lysil residues, corresponding in all three peptides to their 13–20 amino acid region. A predominantly disordered structure was again observed for VIP in aqueous solvents, and zwitterionic lipids, suggesting that the charge of the polar head group plays an important role in helix formation. Using circular dichroism (CD) spectra studies with 40% HFIP/H$_2$O mixture and $^1$H-NMR studies Fournier et al., *Peptides* 5:160–177 (1984), showed that the 15–28 portion of the VIP segment forms an α-helix in the presence of organic solvent. A complete structural study of the native VIP in 40% TFE was performed by Theriault et al., *Biopolymers* 31:459–464 (1991) using two-dimensional $^1$H-NMR spectroscopy. Their results were similar to the ones obtained by Fry et al., *Biochemistry* 28:2399–2409 (1989) who investigated VIP in 25% methanol/water. They described two helical segments between the amino acids 7–15 and 19–27 linked by a random coil peptide chain portion that granted mobility to the molecule.

Finally several groups worked on the development of more potent analogs of VIP as potential therapeutic agents, since the native peptide had a very low bioavailability. Interestingly, all of them modified the sequence of VIP to enhance its helicity and amphiphilicity. VIP structure-activity relationship were studied extensively by Bolin and his collaborators (Fry et al., *Biochemistry* 28:2399–2409 (1989); Bolin et al., *Biopolymers* 37:57–66 (1995). Among their results, the enhancement of the helical structure by specific substitutions of amino acid residues was proportionally related to an increase in potency, and the pharmacoactive functional group of the VIP was found to consist of multiple binding sites throughout the entire peptide sequence. Helix based analogs of VIP were also developed by Musso et al., *Biochemistry* 27:8174–8181 (1988) that showed greater interactions with receptors. Stearyl-Norleucine-VIP analog that has a 100-fold greater potency was designed by Gozes et al., *Endocrinology* 134:2121–2125 (1994), for noninvasive impotence treatment and neurodegenerative diseases Gozes et al. *J. Pharmacol. Exp. Ther.* 273:161–167 (1996). The addition of fatty acid moiety and the amino acid substitutions increased the lipophilicity of the peptide, which was believed to improve biological membrane penetration.

In summary, VIP has been shown to adopt a helical conformation in hydrophobic environments, provided by organic solvent, and the helical structure of the VIP increases with an increase in the hydrophobicity of the environment. This helical motif found in the central part of the peptide, which is rich in basic, hydrophobic residues, forms an amphiphilic structure that may facilitate the binding to receptors and promote direct interactions with membrane lipids, causing an increase in bioactivity. Furthermore, it is possible that the helical structure of VIP also contributes to an increased stability, by protecting specific sites particularly sensitive to proteolytic degradation.

As reviewed by Gozes et al., *Mol. Neurobiol.* 3:201–236 (1989), immunofluorescence and radioimmunoassay techniques demonstrated the wide but selective distribution of VIP in the central and peripheral nervous systems. In the brain, the highest density of VIP-rich neurons occur in the hypothalamus, particularly in the suprachiasmatic and paraventricular nuclei and in the cerebral cortex. VIP concentrations are higher in the hypophyseal portal blood than in the peripheral blood, indicating secretion of the peptide by the hypothalamus and its transport to the adenohypophysis. In the peripheral nervous system, VIP-immunoreactive nerves are found in fibers and terminals that supply blood vessels, nonvascular smooth muscle, and glandular acini and ducts in many organs. Coexistence of VIP with acetylcholine in cholinergic neurons is also well-documented. Some VIP nerves have recently been acknowledged to be components of the autonomic nervous system. Furthermore, Muller et al., *Mol. Neurobiol.* 10: 115–134 (1995) showed that a distinct groups of cells, such as platelets, mast cells, skin cells, neutrophils, and retinal amacrine cells appear to be able to synthesize and release VIP.

The physiologic effects of VIP are largely mediated by its binding to specific cell receptors. Hirata et al., *Biochem. Biophys. Res. Comm.* 132:1079–1087 (1985) described two specific receptor binding sites for VIP, one low-, one high-affinity, on cultured vascular smooth muscle cells from rat aorta, that were distinct from β-adrenergic receptors. From a molecular aspect two distinct polyvalent VIP receptors were distinguished after cloning of cDNAs. The first, $VIP_1$ receptor is similar to the secretin receptor also called PACAP type II receptor, is expressed in intestine, lung, liver, muscle cells, ovaries, and various brain regions (Sreedharan et al., *Biochem. Biophys. Res. Comm.* 203:141–148 (1994)). The second, $VLP_2$ receptor is closer to the GRF binding site and has a distinct distribution in the central nervous system (Lutz et al., *FEBS Let.* 334:3–8 (1993)). Recent studies have also indicated that VIP action can be non-receptor mediated (Séjourné et al., *Am. J. Physiol.* 273:R287–R292 (1997)).

Although studied for many years, most of the intracellular signaling cascades of VIP remain to be elucidated. Most common cellular action observed in many cells is the increased production of intracellular cyclic adenosine monophosphate (cAMP), via the stimulation of adenylate cyclase. The subsequent steps of cAMP-induced pathways are still highly speculative. Conversely, several observations indicate the existence of cAMP-independent signal transduction cascades. Sreedharan et al., *Biochem. Biophys. Res. Comm.* 203:141–148 (1994) recently found that $VIP_1$ receptor induced two separate pathways in one cell type, i.e. activation of adenylate cyclase and increase in intracellular $Ca^{2+}$. Stimulation of adrenal medulla and cervical ganglion by VIP were shown to increase the generation of inositol 1,4,5 triphosphate ($IP_3$) and intracellular $Ca^{2+}$ (Malhotra et al., *J. Biol. Chem.* 263:2123–2126 (1988)). Moreover, it has been proposed that internalized VIP could bind to nuclear receptors and activate protein kinase C (Omary et al., *Science* 238:1578–1580 (1987); Zorn et al., *Biochem. Pharmacol.* 40:2689–2694 (1990)).

The pleiotropic distribution of VIP is correlated with its involvement in a broad spectrum of biological activities, and growing evidence suggests that VIP plays a major role in regulating a variety of important functions in many organs. Physiological actions of VIP have been reported on the cardiovascular, respiratory, reproductive, digestive, immune, and central nervous systems, as well as metabolic, endocrine and neuroendocrine functions (for review, Said, *Trends Endocrinol. Metab.* 2:107–112 (1991)). In many cases, VIP acts as a neurotransmitter or neuromodulator and is released into the local circulation at small concentrations. Among the functions that VIP is believed to mediate or promote (Said, *Trends Endocrinol. Metab.* 2:107–112 (1991) Paul et al., *Neurochem. Int.* 23:197–214 (1993)), are vasodilation of cerebral, coronary, peripheral, and pulmonary blood vessels, linked to the regulation of vascular tone; the relaxation of gastrointestinal, uterine, and tracheobronchial smooth muscles; exocrine secretion, water and anions by intestinal, respiratory, and pancreatic epithelia; stimulation of the male and female activity and responses; release and regulation of neuroendocrine functions (renin release, melatonin secretion); inhibition of the immune system (inhibition of platelet aggregation); and stimulation and protection of neuronal cells.

New VIP functions such as inhibition of vascular smooth muscle cell growth, proliferation of cultured human keratinocytes, the release of neutrophic and growth factors involved in cell differentiation and ontogeny, and antioxidant properties have been recently proposed but still need additional studies (Muller et al., *Mol. Neurobiol.* 10:115–134 (1995); Said, *Trends Endocrinol. Metab.* 2:107–112 (1991)).

Some human diseases today are known to be associated with the deficiency in the release of VIP. The deficiency of VIP has been linked to the pathogenesis of several diseases, such as cystic fibrosis, diabetic impotence, congenital mengacolon in Hirschsprung's disease, and achalasia of the esophagus. Furthermore, VIP insufficiency may be a cause of bronchial hyperactivity in asthmatic airways since VIP is known to mediate airway relaxation in humans, and lung tissues of asthmatic patients showed a selective absence of VIP nerves (Ollerenshaw et al., *N. Engl. J. Med.* 320:1244–1248 (1989)). Finally, Avidor et al., *Brain Res.* 503:304–307 (1989) observed an increase in brain VIP gene expression in a rat model for spontaneous hypertension, thought to be associated with the pathophysiology of the disease.

On the other hand, the excessive release of VIP has been linked to the pathogenesis of few diseases. One of the pathological syndromes is pancreatic cholera, a watery diarrhea-hypocholaremia-hypochloridria condition (Krejs, *Ann. N.Y. Acad. Sci.* 527:501–507 (1988)). Certain tumors, especially pancreatic, bronchogenic, and neurogenic, have been associated with elevated circulatory levels of VIP.

Due to the numerous physiological actions of VIP, the use of VIP as a drug has been of growing interest. The potential therapeutic developments of VIP include treatment of diseases where regional blood flow is deprived. These include hypertension by reducing systemic vascular overload, left ventricular failure, congestive heart failure, and coronary or peripheral ischemia. VIP infusion in man for 10 hours was shown to reduce total peripheral resistance by 30% and increase forearm blood flow by 270% (Frase et al., *Am. J. Cardiol.* 60:1356–1361 (1987)). Moreover, Smiley, *Am. J. Med. Sci.* 304:319–333 (1992) showed VIP-immunoreactive nerves in the skin and plasma levels of VIP were found to be low in patients with schleroderma, thus treatment with VIP may restore this impaired response. Other diseases which could be treated by administration of VIP include treatment of asthmatic bronchospasm. VIP has been shown to protect against bronchoconstriction in asthmatic patients and as a relaxant of tracheobronchial smooth muscle (Morice et al., *Lancet* 26 2(8361): 1225–1227 (1983)). Its anti-inflammatory properties could further enhance its therapeutic value in asthma (Said, *Biomed. Res.* 13 (Suppl. 2):257–262 (1992)). Administration of VIP could also be used in the prevention and/or reduction of tissue injury. The peptide has been described to prevent neuronal cell death produced by the external envelope protein gp120 of the human immunodeficiency virus in vitro (Gozes et al., *Mol. Neurobiol.* 3:201–236 (1989); Hökfelt, *Neuron.* 7:867–879 (1991)), which may lead to a potential therapy for AIDS dementia as well as treatment of Alzheimer's disease. Likewise, the acute inflammatory lung injury induced by a variety of insults including oxidant stress was diminished by the presence of VIP (Berisha et al., *Am. J. Physiol.* 259:L151–L155 (1990)). VIP added to certain pneumoplegic solutions was also shown to improve rat lung preservation before transplantation (Alessandrini et al., *Transplantation* 56:964–973 (1993)).

A major factor limiting in vivo administration of VIP has been its reduced bioavailability at target tissues mostly because of proteolytic degradation, hydrolysis, and/or a multiplicity of conformations adopted by the peptide. It has been speculated that intracellular delivery of VIP alone and/or VIP-calmodulin mixtures could bypass the requirement for cell-surface binding of the peptide and thus enhance the biological actions of the peptide. Provision of the peptides expressed in and on liposomes would possibly permit intracellular delivery, since lipid bilayers of liposomes are known to fuse with the plasma membrane of cells and deliver entrapped contents into the intracellular compartment.

Liposomes are microscopic spherical structures composed of phospholipids which were first discovered in the early 1960s (Bangham et al., *J. Mol. Biol.* 13:238 (1965)). In aqueous media, phospholipid molecules being amphiphilic spontaneously organize themselves in self-closed bilayers as a result of hydrophilic and hydrophobic interactions. The resulting vesicles, called liposomes, therefore encapsulate in their interior part of the aqueous medium in which they are suspended, a property that makes them potential carriers for biologically active hydrophilic molecules and drugs in vivo. Lipophilic agents could also be transported, embedded in the liposomal membrane. However, the success of liposomes in medical applications has been severely limited by their rapid sequestration in the reticuloendothelial system (RES). Efforts to reduce the RES uptake of liposomes led in the late 1980s to the development of liposomes with a significant increase in their circulation half-lives (sterically stabilized liposomes) (SSL), and revived hopes for their development as drug delivery systems. Two independent laboratories, from studying the biology of red blood cells, identified the presence of sialic acid on the membrane of erythrocytes to be partly responsible for their very long circulation times. Indeed, the incorporation of sialated glycolipids such as the ganglioside $GM_1$ into phosphatidylcholine (PC):cholesterol (Chol) liposomes effectively increased the circulation time of the vesicles (Allen et al., *FEBS Letter* 223:42–46 (1987); Allen et al., U.S. Pat. No. 4,920,016, Appl. 132,136, Dec. 18, 1987; 24 pp, Apr. 24, 1990; Gabizon et al., *Proc. Natl. Acad. Sci. USA* 8:6949 (1988)). These first results have raised new perspectives for liposomes as drug carriers, especially in the field of chemotherapy, since longer half-lives correlated well with higher uptake by implanted tumors in mice (Gabizon et al., *Proc. Natl. Acad Sci. USA* 8:6949 (1988)).

In the 1990s, the near simultaneous development by several investigators of the second generation of SSL containing lipid derivatives of polyethylene glycol (PEG) resulted in further improvements (Klibanov et al., *FEBS Letter* 268 (1):235–237 (1990); Allen et al., *Biochim. Biophys. Acta* 1066:29–36(1991)). Klibanov et al., *FEBS Letter* 268 (1):235–237(1990) demonstrated that the blood clearance half-life of PC/Chol (1:1) liposomes in mice was 30 min vs. 5 hours for vesicles composed of PC/Chol/PEG-PE (1:1:0.15). Besides, the preparation techniques of the conjugated phospholipid PEG-di-steroyl-phosphatidylethanolamine (DSPE) were reported to be quick and simple (Klibanov et al., *FEBS Letter* 268 (1):235–237 (1990); Allen et al., *Biochim. Biophys. Acta* 1066:29–36 (1991), and PEG had already received approval for pharmaceutical use (PEG-ADA, Rhinaris®).

Of interest to the present invention is the observation of increased half-life of circulating protein through conjugation of the protein to a water soluble polymer [Nucci, et al., *Adv. Drug Del. Rev.* 6:133–151 (1991); Woodle, et al., *Proc. Intern. Symp. Control. Rel. Bioact. Mater.* 17:77–78 (1990)]. This observation led to the development of sterically stabilized liposomes (SSL) (also known as "PEG-liposomes") as an improved drug delivery system which has significantly minimized the occurrence of rapid clearance of liposomes from circulation. [Lasic and Martin, *Stealth Liposomes*, CRC Press, Inc., Boca Raton, Fla. (1995)]. SSL are polymer-coated liposomes, wherein the polymer, preferably polyethylene glycol (PEG), is covalently conjugated to one of the phospholipids and provides a hydrophilic cloud outside the vesicle bilayer. This steric barrier delays the recognition by opsonins, allowing SSL to remain in circulation much longer than conventional liposomes [Lasic and Martin, *Stealth Liposomes*, CRC Press, Inc., Boca Raton, Fla. (1995); Woodle, et al., *Biochem. Biophys. Acta* 1105:193–200 (1992); Litzinger, et al., *Biochem. Biophys. Acta* 1190:99–107 (1994); Bedu Addo, et al., *Pharm. Res.* 13:718–724 (1996)] and increases the pharmacological efficacy of encapsulated agents, as demonstrated for some chemotherapeutic and anti-infectious drugs [Lasic and Martin, *Stealth Liposomes*, CRC Press, Inc., Boca Raton, Fla. (1995)]. Studies in this area have demonstrated that different factors affect circulation half-life of SSL, and ideally, the mean vesicle diameter should be under 200 nm, with PEG at a molecular weight of approximately 2,000 Da at a concentration of 5% (9–12) [Lasic and Martin, *Stealth Liposomes*, CRC Press, Inc., Boca Raton, Fla. (1995); Woodle, et al., *Biochem. Biophys. Acta* 1105:193–200 (1992); Litzinger, et al., *Biochem. Biophys. Acta* 1190:99–107 (1994); Bedu Addo, et al., *Pharm. Res.* 13:718–724 (1996)].

The mechanism by which SSL avoids macrophages and circulate longer in the blood is thought to involve the formation of a "steric barrier" around the liposomes by the attached PEG molecules. Torchilin, et al., *Stealth Liposomes*, D. Lasic and F. Martin (Eds.), CRC Press, Boca Raton, Fla., pp. 51–62 (1995) claimed that the ability of PEG to prevent liposome opsonization is determined by its behavior in the solvent which entails the formation of a hydrophilic cloud over the vesicle surface even at relatively low polymer concentrations. This negative, hydrophilic coat would act as a protective shield delaying the binding of opsonins that are often attracted to the positive charged lipid surfaces.

The circulation time of sterically stabilized liposomes may be controlled by selection of their size, PEG molecular weight, chain length and concentration and selection of the lipid composition. Maruyama et al., *Chem. Pharm. Bull.* 39:1620–1622 (1991) tested SSL with different PEG molecular weights (1,000, 2,000, 5,000, and 12,000 Da), with a constant size (180 to 200 nm) and composition (6% DSPE-PEG in DSPC/Chol (1:1)). The $PEG_{2,000}$-liposomes appeared to be the longest lasting formulation in mice, with 47.1% of injected dose after 6 h still in the blood. Klibanov et al., *FEBS Letter* 268 (1):235–237 (1990) conducted similar studies on mice with PC/Chol/PEG-PE (10:5:1) extruded liposomes of 200 nm diameters, using $PEG_{750}$, $PEG_{2,000}$ and $PEG_{5,000}$. The authors evaluated the "degree of steric barrier" produced on the liposome surface and concluded that it was directly correlated to chain length of PEG and concentration-dependent. They suggested that the SSL prolongation was directly proportional to PEG chain length, which, itself, corresponded to the steric barrier. Finally, other groups (Allen et al., *Biochim. Biophys. Acta* 1066:29–36 (1991); Woodle et al., *Biochim. Biophys. Acta* 1105:193–200 (1992)) found somewhat contradictory results showing that the extension of PEG chain length from 2,000 to 5,000 Da had no additional suppression effect on RES uptake. PEG of molecular weights 1,900, 2,000 and 5,000 have been recently used in various applications.

Huang's group (Klibanov et al., *Biochim. Biophys. Acta* 1062:142–148 (1991); Litzinger et al., *Biochim. Biophys. Acta* 1190:99–107 (1994) pointed out the importance of the size of liposomes in biodistribution studies, and observed that small vesicles (<100 nm) were taken up by the liver, whereas larger ones (300 nm<diameter<500 nm) accumulated in the spleen, particularly in the red pulp and marginal zone. Indeed, the major function of the spleen is to filter the aged or damaged red blood cells, and the liposome uptake was shown to use this same filtration mechanism, followed by splenic macrophage endocytosis. The reason for such an uptake is however unknown. Their studies showed an optimized circulation time for SSL of 150–200 nm diameters. Ghosh et al., *Stealth Liposomes*, D. Lasic and F. Martin (Eds.), CRC Press, Boca Raton, Fla., pp. 13–24 (1995) confirmed this work, showing the limitation of the prolongation effect of SSL to a narrow size range, between 70 and 200 nm diameter. Most of SSL applications seem indeed to include a size reduction step in their liposome preparation methods.

Klibanov et al., *Biochim. Biophys. Acta* 1062:142–148 (1991) studied the effect of the lipid composition on the blood circulation time of SSL, and found that the half-lives of different SSL were all very close, except when phosphatidylserine (PS) was added. Woodle et al., *Biochim. Biophys. Acta* 1105:193–200 (1992) also conducted biodistribution studies on mice and rats with SSL of various lipid compositions. They showed similarly that an increase in the hydrogenation of PC (i.e. bulk lipid transition temperature), the addition of the anionic lipid PG, and different levels of cholesterol had no impact on the prolongation effect. A consistent half-life of about 15 hours for blood clearance was observed, regardless of the phospholipid's phase transition, cholesterol content or neutral/negative charges.

Nevertheless, Bedu-Addo et al., *Pharm. Res.* 13:718–724 (1996) recently shed light on the role of cholesterol in the stabilization of liposomes, claiming that the most suitable formulation for prolonged circulation times should contain a minimum of 30 mol % cholesterol, with low concentrations of short-chain PEG-PE (<10%). The authors investigated the efficiency of surface protection in vitro using a fluorescence energy transfer technique. The addition of cholesterol improved surface protection, due to the increase in bilayer cohesive strength. It would limit the formation of "bald spots" less enriched with PEG-PE in the liposomal bilayer, thus inhibiting phase separation and lipid exchange with blood lipoproteins. However, in vivo, it was shown that the long-lasting circulation of SSL seems to depend mostly on the PEG coating and less on the liposome bilayer composition.

Different investigators reported that only 5% PEG-PE could give an optimized steric barrier effect on the vesicles (Klibanov et al., *Biochim. Biophys. Acta* 1062:142–148 (1991); Woodle et al., *Biochim. Biophys. Acta* 1 105:193–200 (1992); McIntosh et al., *Stealth Liposomes*, D. Lasic and F. Martin (Eds.), CRC Press, Boca Raton, Fla., pp. 63–71 (1995)). A maximal limit of 10 mol % PEG was very recently proposed to obtain adequate results from in vitro studies, because of the spontaneous formation of micelles of PEG-PE at higher concentrations (Bedu-Addo et al., *Pharm. Res.* 13:718–724 (1996)).

Also of interest to the present application is the disclosure of PCT Application PCT/US97/05161 relating to improvements in sterically stabilized liposomes and therapeutic and diagnostic including acoustic diagnostic methods of using same.

Of interest to the present invention is work relating to molecular aggregates called "micelles" which are defined as colloidal aggregates spontaneously formed by amphiphilic compounds in water above a critical solute concentration, the critical micellar concentration (CMC), and at solution temperatures above the critical micellar temperature (CMT). The molecules constituting the micelles are in rapid dynamic equilibrium with the unassociated molecules. The increase in the concentration above the CMC usually leads to an increase in the number of micelles without any change in micellar size; however, in certain cases with phospholipid mixed micelles, the spherical micelles enlarge into rod-shaped micelles (Carey et al., *Arch. Inter Med.* 130:506–527 (1972); Hjelm, Jr. et al., *J. Phys. Chem.* 96 (21):8653–8661 (1992)). The CMC is strongly temperature dependent, and at a given concentration the monomer to micelle transition occurs gradually over a broad temperature range (Almgren et al., *Colloid Polym. Sci.* 273:2–15 (1995)). An increase in the temperature leads to an increase in the number of aggregates, while the hydrodynamic radius remains constant (Nivaggioli et al., Langmuir. 11 (3):730–737 (1995); Alexandridis et al., *Langmuir.* 11: 1468–1476 (1995)). In general the increase in temperature leads to an increase in hydrophobic interactions and the water dielectric constant is reduced augmenting the ionic repulsion forces. There are many ways to determine the CMC of an amphiphilic compound (surface tension measurements, solubilization of water insoluble dye, or a fluorescent probe, conductivity measurements, light scattering, and the like). According to a preferred method, surface tension measurements may be used to determine the CMC of PEG-DSPE micelles at room temperature.

Surfactant micelles are used as adjuvants and drug carrier systems in many areas of pharmaceutical technology. Micelles have been used to increase bioavailability or decrease adverse effects of the drugs (Trubetskoy et al., *Advan. Drug Deliv. Reviews* 16:311–320 (1995). In addition, the small size of micelles play a key role in transport across membranes including the blood brain barrier (Muranushi et al., *Chemistry and Physics of lipids* 28:269–279 (1981); Saletu et al., *Int. Clin. Psychopharmacol.* 3:287–323 (1988). The surfactant micelles are thermodynamically unstable in aqueous media and subject to dissociation upon dilution. Yokoyama et al., *Makromol Chem. Rapid Commun.* 8:431–435 (1987) proposed a class of amphiphilic polymers, such as polyethylene glycol (PEG), which are known to form more stable polymeric micelles in aqueous solutions. There are many advantages to polymeric micelles, such as small size might control penetration across physiological barriers, increases the half-life in vivo, and allows to target micelles to specific tissues.

Studies involving polymer conjugated lipid micelles, such as PEG conjugated to PE are very recent. In one such study, where polyethyleneoxide (PEO) is conjugated to PE and dissolved in aqueous media forming micelles. The study performed by Trubetskoy et al., *Acad. Radiol.* 3:232–238 (1996) used PEO-PE conjugated lipid to encapsulate indium-111 and gadolinium chalets as contrast media for precutaneous lymphography using magnetic resonance imaging (MRI) topography. The study concluded that PEO-PE micelles can incorporate amphiphilic agents and prolong their actions in vivo by avoiding the RES, and prolonging the circulation period.

The stability of amphiphilic micelles depends on the strength of Van der Waals interactions. The polymer presence on the micellar surface contributes to its steric protection by repulsive action of the hydrophilic layer from the hydrophobicity of macrophages, thus decreasing the uptake by reticuloendothelial system (RES). Furthermore, the negative charge of the polymer creates a repulsive steric effect in vivo that prevents the binding of opsonins, plasma protein that facilitates RES uptake (Trubetskoy et al., *Proceed. Intern. Symp. Control. Rel. Bioact. Mater.* 22:452–453 (1995)). Thus, the polar and electrostatic interactions of the polymer with the in vivo environment is responsible for the steric stabilization of phospholipid micelles in vivo.

For sterically stabilized phospholipid micelles (SSM) formation an optimal amphiphilic compound is required, one with the right amount of hydrophobicity and hydrophilicity. Factors such as molecular weight and chain length of polymer, size, lipid concentration, and polymer concentrations may play a very important role in determination of the optimal micellar formulation. However, so far there have been no phospholipid micelles studies performed that evaluate the parameters for optimal formulation and activity.

Conversely, many studies of block copolymer, amphiphilic polymers, micelles have been done. Nivaggioli et al., *Langmuir.* 11 (3):730–737 (1995) tested block copolymer micelles of different pluronic copolymers (PEO-PPO-PEO) at a constant temperature and concentrations. The authors found that the increase in the molecular weight of the copolymer leads to an increase in the hydrodynamic size, thus suggesting an increase in the hydrophobic core size. Thus, the increase in micelle size due to the molecular weight and chain length would lead to an increase in uptake by RES. Therefore, high molecular weight and chain length decreases circulation time and hence the half-life of the SSM. Overall, the authors found PEO to be the most promising copolymer for SSM stability. Moreover, Carey and co-workers have determine that significant increase in the polymer concentration above the CMC leads to the formation of rod-like micelles causing an increase in the viscosity of the solution (Carey et al., *Arch. Inter Med.* 130:506–527 (1972); Almgren et al., *Colloid Polym. Sci.* 273:2–15 (1995)). Therefore, the elongated micelles increase the hydrophobicity of the micelles and may allow more of the non-polar drug to be encapsulated.

From these block co-polymers, amphiphilic compounds, one can infer that the study of parameters that optimize the formulation and activity of phospholipid micelle stability to be very relevant, and should be considered in the future.

The utilization of SSM as drug delivery system is a fairly new application, especially as therapeutic and diagnostic agents. As Trubetskoy et al., *Proceed. Intern. Symp. Control. Tel. Bioact. Mater.* 22:452–453 (1995) pointed out, almost every possible drug administration route has benefitted from the use of micellar drug formation in terms of increased bioavailability or reduced adverse effects. The small size of the micellar formulation allows for their penetration of blood brain barrier making it an ideal carrier for treatment of CNS diseases, such as Alzheimer's disease. Recently, SSM have been used as diagnostic agents using MRI and STM techniques (Trubetskoy et al., *Proceed. Intern. Symp. Control. Test. Bioact. Mater.,* 22:452–453 (1995); Zareie et al., *Collids and Suraces A: Physiocochemical and Engineering Aspects.* 112:19–24 (1996)). In both cases SSM were incorporation with either a dye or paramagnetic agents followed by parenteral administration and visualization. In both cases the half-life of the SSM was at least 2 hours.

Also of interest to the present invention is the disclosure of Friedman et al., U.S. Pat. No. 5,514,670 which relates to submicron emulsions for delivery of bioactive peptides including vasoactive intestinal peptide analog. The submicron particles are said to have a weighted average diameter of 10 to 600 nm, more preferably 30 to 500 nm and most preferably 70 to 300 nm.

Of further interest to the present invention is calmodulin (CaM) which is an ubiquitous 17 kd protein that is found widely in the body and has many functions. Calmodulin functions mainly as a regulatory protein and serves as a sensor for calcium ions. The binding of calcium ions ($Ca^{+2}$) to four sites in calmodulin induces the formation of $\alpha$-helix and other conformational changes that convert it from an inactive to an active form. The activated calmodulin in turn binds to many enzymes and proteins in the cell and modifies their activity. The globular structure of CaM hides hydrophobic binding sites for proteins that are exposed upon CaM interactions with $Ca^{+2}$ ions and/or membrane phospholipids (Chiba et al., *Life Sciences* 47:953–960 (1990); Damrongehai et al., *Bioconjugate Chem.*, 6:264–268 (1995)). Bolin, *Neurochem. Int.* 23:197–214 (1993) found that VIP is a potent stimulant of $Ca^{+2}$ binding to calmodulin suggesting a correlation of VIP interactions with CaM and specific cellular regulatory activities.

Paul et al., *Neurochem. Int.* 23:19714 214 (1993) also reported that internalized VIP had the ability to directly bind to calmodulin (CaM), and that it inhibited both phosphodiesterase as well as the calmodulin-dependent myosin light chain kinase activity. This observation supports a functional role for VIP-CaM complex (Stallwood et al., *J. Biol. Chem.* 267:19617–19621 (1992); Shiraga et al., *Biochem. J.* 300:901–905 (1994), therefore suggesting that calmodulin, a multifunctional protein responsible for the regulation of many different signaling enzymes, could be an intracellular receptor for VIP (Paul et al., *Neurochem. Int.* 23:197–214 (1993). Thus, VIP may regulate signal transduction by CaM association. Moreover, CaM is also found in extracellular fluid and cerebrospinal fluid and that it is actively secreted by cells (Paul et al., *Neurochem. Int.* 23:197–214 (1993)), thus the VIP-Cam complex may protect the peptide from protease digestion. $Ca+^2$ ions and lipids are known to effect the peptide-CaM interactions. VIP and $Ca^{+2}$ binding by CaM is cooperative, in that calcium ion binding to receptors facilitates VIP binding to CaM and vise versa. Phospholipase treatment has been shown to inhibit VIP binding in intact membranes and modulates the binding by solubilizing VIP-binding protein fractions (Paul et al., *Ann. N. Y. Acad. Sci.* 527:282–295 (1988)). Thus, the biochemical consequences of VIP-CaM binding depends on the identity of CaM binding site, and conformational changes induced by VIP-CaM binding.

Thus, there exists a need in the art to provide further improvements in the use of micelle technology for the therapeutic and diagnostic administration of bioactive molecules. More specifically, there remains a desire in the art for improved methods for administration of amphipathic peptides including, but not limited to, members of the VIP/GRF family of peptides associated with phospholipids in order to achieve a more prolonged and effective therapeutic effect.

SUMMARY OF THE INVENTION

The present invention provides improved methods of preparing biologically active micelle products comprising one or more biologically active amphipathic compounds in association with a micelle. As used herein, compounds embrace peptides, proteins, enzymes in general, as well as fragments, analogs, and modulators thereof With respect to proteins, the invention contemplates use of both L and D forms. Where compounds of the invention exist in both cis and trans conformations, the invention comprehends use of either form alone or a combination of both forms. The micellar formulations of the invention deliver and enhance bioactivity of the biologically active peptides in a manner which provides improvements in the efficacy and duration of the biological effects of the associated peptides. Increased efficacy and duration of the biological effect is believed to result, at least in part, from interaction of the compound with the micelle in such a manner that the compound attains, and is maintained in, an active or more active conformation than the compound in an aqueous environment. The invention thus overcomes the problems associated with previous liposomal formulations, such as, but not limited to, uptake by the reticuloendothelial system, degradation of the compound, or delivery of the compound in an inactive conformation. According to one aspect of the present invention, polyethylene-glycol (PEG) is covalently conjugated to DSPE and used to form polymeric micelles which are then passively loaded with VIP. The PEG-DSPE forms micelles with a hydrophobic core consisting of distearoyl phosphatidylethanolamine (DSPE) fatty acid chains which is surrounded by a hydrophilic "shell" formed by the PEG polymer.

According to one aspect of the invention, a method is provided for preparing a biologically active micelle product comprising one or more biologically active amphipathic compounds in association with a micelle; said method comprising the steps of a) mixing a combination of one or more lipids wherein said combination includes at least one lipid component covalently bonded to a water-soluble polymer; b) forming sterically stabilized micelles from said combination of lipids; and c) incubating micelles from step b) with one or more biologically active amphipathic compounds under conditions in which said compound become associated with said micelles from step b) in a more biologically active conformation as compared to the compound in an aqueous solution. According to a further aspect of the invention, a biologically active micelle product may be produced by the coprecipitation of a biologically active amphipathic compound with lipids to form micelles with incubation not required. Specifically, a method is provided of preparing a biologically active micelle product comprising one or more biologically active amphipathic compound in association with a micelle; said method comprising the steps of: a) mixing one or more lipids wherein said combination includes at least one lipid component covalently bonded to a water-soluble polymer with a biologically active amphipathic compound; b) forming sterically stabilized micelles from the mixture of step (a) under conditions in which said compound becomes associated with said micelles in an active conformation.

As one aspect of the invention, the micelles are sterically stabilized micelles (SSM) which are produced from a combination of lipids which includes at least one lipid component covalently bonded to a water-soluble polymer. This polymer bound phospholipid is the micelle forming component. Other lipids are actually solubilized in this micelle to form mixed micelles. The water-soluble polymer, which is preferably polyethylene glycol (PEG) increases the lipid solubility to form micelles instead of vesicles in aqueous media. It also acts to sterically stabilize the resulting micelle against uptake by components of the reticuloendothelial system.

In another aspect, the invention provides a method for preparing a biologically active sterically stabilized micelle product comprising one or more biologically active amphipathic compounds, said method comprising the steps of: a) preparing a mixture of an aqueous solution with one or more lipids wherein at least one lipid is conjugated to a water soluble polymer; b) forming sterically stabilized micelles; c) mixing said micelles with one or more amphipathic compound(s); d) incubating said micelles and said amphipathic compound(s) under conditions wherein the amphipathic compound(s) assumes a more favorable biologically active conformation upon association with said micelle as compared to the compound in an aqueous solution.

In another aspect, the invention provides a method for preparing a biologically active sterically stabilized micelle product comprising one or more biologically active amphipathic compounds, said method comprising the steps of: a) dissolving in an organic solvent one or more lipids wherein at least one lipid is conjugated to a water soluble polymer; b) removing the organic solvent to leave a dry lipid film; c)

hydrating the dry lipid film with an aqueous solution; d) forming sterically stabilized micelles; e) combining said micelles with one or more amphipathic compounds; and f) incubating said micelles and said amphipathic compound(s) under conditions wherein the amphipathic compound(s) assumes a more favorable biologically active conformation upon association with said micelle as compared to the compound in an aqueous solution.

In another aspect, the invention provides a method for preparing a biologically active sterically stabilized micelle product comprising one or more biologically active compounds and one or more targeting compounds; said method comprising the steps of: a) dissolving in an organic solvent said biologically active compound(s) and one or more lipids wherein at least one lipid is conjugated to a water soluble polymer; b) removing the organic solvent to leave a dry film; c) hydrating the dry film with an aqueous solution; d) forming sterically stabilized micelle products; e) combining said micelle products with one or more targeting compounds; and f) incubating said micelle products under conditions wherein the targeting compound(s) associates with said micelle products. In one aspect, the targeting compound is linked to one or more lipid components of the micelle. Preferably linkage between the targeting compound and the lipid is effected by covalent means in a manner that permits the targeting compound to interact with its cognate receptor, ligand, or binding partner and position the micelle in close proximity.

The methods of the invention are useful with any biologically active amphipathic compound, peptide, protein, or fragment, analog, or modulator thereof which can thereby be stably maintained in an active conformation in association with or within the lipid core of the micelle. Preferred amphipathic compounds include those characterized by having one or more α or π-helical domains in their biologically active conformation and particularly those in which polar and apolar residues are separated on opposite sides of the helix. Particularly preferred amphipathic compounds useful with the invention include any member of the vasoactive intestinal peptide (VIP)/growth hormone releasing factor (GRF) family of peptides which includes biologically active analogs thereof The mammalian and non-mammalian VIP/GRF family of peptides includes functional analogs of VIP and GRF, peptide histidine isoleucine (PHI), peptide histidine methionine (PHM), growth hormone releasing factor (GRF), pituitary adenylate cyclase activating peptide (PACAP), secretin, and glucagon. Like VIP, other members of the VIP/GRF family of peptides, and biologically active analogs thereof, can form amphipathic helices wherein hydrophobic and hydrophilic domains of the peptide are segregated and the hydrophobic domain(s) is capable of binding lipid core. The invention also contemplates modulators having enhanced bioactivity in association with micelles prepared by a method of the invention. A particularly preferred peptide for use according to the invention is VIP. Preferred micelles according to the invention are characterized by an average diameter of less than about 20 nm. According to one aspect of the invention the micelles further comprise calmodulin. The biologically active peptide products of the invention may be utilized in a wide variety of therapeutic, diagnostic, cosmetic and organ, tissue and cell preservative uses wherein it is desired to deliver a high level of biologically active compound or to detect targeted delivery of the micelle product as will be described below.

In another aspect, the invention provides methods for preparing a biologically active sterically stabilized crystalline product comprising one or more biologically active compounds which are insoluble in an aqueous solution; said method comprising the steps of a) dissolving in an organic solvent said biologically active compound(s) and one or more lipids wherein at least one lipid is conjugated to a water soluble polymer; b) removing the organic solvent to leave a dry film; c) hydrating the dry film with an aqueous solution; and d) forming a sterically stabilized crystalline product. As used herein and in subsequently described crystalline products of the invention, "insoluble" is defined according to the U.S. Pharmacopeia National Formulary [USP 23, 1995, page 10], as requiring 10,000 or more parts of solvent for 1 part of solute. The crystalline product of the method is essentially a micelle-encased aggregate of the insoluble compound which is densely packed and crystallized.

In still another aspect, the invention provides methods for preparing a biologically active sterically stabilized crystalline product comprising one or more biologically active compounds which are insoluble in an aqueous solution; said method comprising the steps of: a) dissolving in an organic solvent said biologically active compound and one or more lipids wherein at least one lipid is conjugated to a water soluble polymer; b) freeze-drying to remove the organic solvent; c) hydrating with an aqueous solution; and d) forming a sterically stabilized crystalline product.

In still another aspect, the invention provides methods for preparing a biologically active sterically stabilized crystalline product comprising one or more biologically active compounds which are insoluble in aqueous solution and one or more amphipathic targeting compounds; said method comprising the steps of: a) dissolving in an organic solvent said biologically active compound(s) and one or more lipids wherein at least one lipid is conjugated to a water soluble polymer; b) removing the organic solvent to leave a dry film; c) hydrating the dry film with an aqueous solution; d) forming sterically stabilized crystalline products; e) combining said crystalline products with one or more targeting compounds; and f) incubating said crystalline products under conditions wherein the targeting compound(s) associates with said crystalline products, said targeting compound conjugated to a lipid of the micelle.

Methods of the invention for producing sterically stabilized crystalline products are amenable to the use of any compound that is insoluble in an aqueous solution. Preferred insoluble compounds include, but are not limited to, progesterone, testosterone, estrogen, prednisolone, prednisone, 2,3 mercaptopropanol, amphotericin B, betulinic acid, camptothecin, diazepam, nystatin, propofol, cyclosporin A, doxorubicin, and Taxol®. In methods of the invention for producing sterically stabilized crystalline product further comprising one or more targeting compounds, any targeting compound that assumes or maintains a biologically active conformation when in association with the sterically stabilized crystalline product can be used. In a preferred embodiment, any of the amphipathic compounds as described above are utilized. In a most preferred embodiment, the targeting compound is VIP or other member of the VIP/GRF family or proteins.

Composition comprising the biologically active micelle product of the invention include those wherein the biologically active amphipathic peptide, protein, fragment, analog, or modulators thereof has an activity selected from the group consisting of anti-oxidant activity, anti-pain, anti-inflammatory, wound healing activity, anti-microbial, antibronchospasm, metabolic activity, anti-cancer activity, cardiovascular activity, antiglaucoma activity, anti-apoptosis, anti-wrinkling activity, cryopreservation, and anti-aging activity. Compositions of the invention include cosmetic, therapeutic and diagnostic compositions. In the case of diagnostic compositions, the micelle product further comprises a detectable label selected from the group consisting of a fluorescent label, a radioactive label, a dye, a gas, and a compound which enhances radiographic, magnetic resonance, and ultrasound imaging.

DETAILED DESCRIPTION OF THE INVENTION

Figure 1:
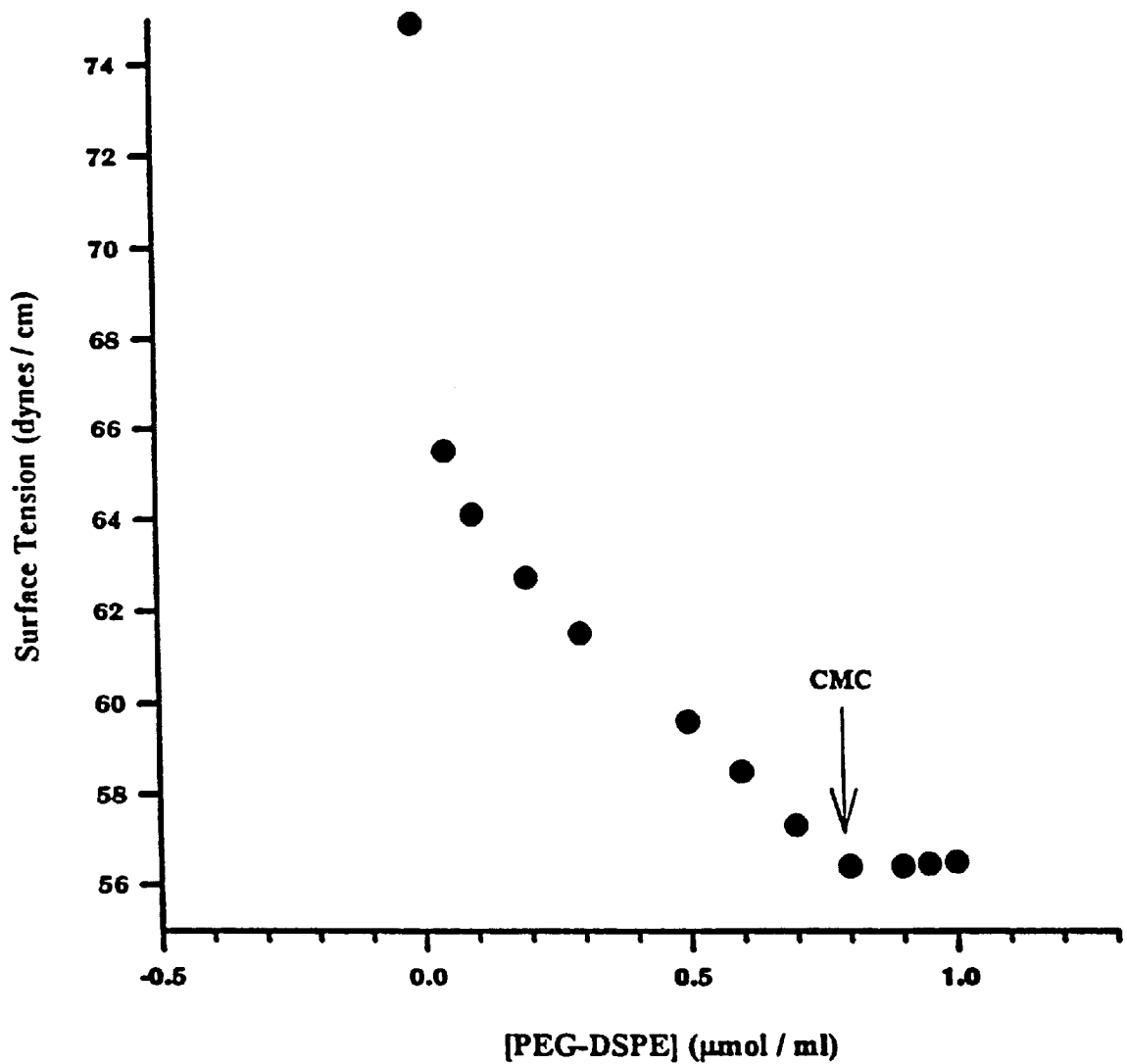
FIG. 1 depicts surface tension measurements of a PEG-DSPE aqueous solution to determine the critical micelle concentration (CMC) at room temperature.

The present invention provides improved methods of preparing biologically active micelle products comprising biologically active amphipathic compounds in association with a micelle. The invention also provides method for preparing sterically stabilized crystalline products comprising compounds that are insoluble in an aqueous solution. The crystalline products of the invention are prepared alone or in combination with a targeting compound. It is preferred that the targeting compound is an amphipathic compound that assumes a more favorable biological conformation in association with the crystalline product. The preferred amphipathic compounds are characterized by having hydrophilic and hydrophobic domains segregated to the extent that the hydrophobic domain is capable of associating within the micellar core. Compounds of the invention preferably attain a biologically active conformation in association with or within the micelle core. More biologically active conformations are those in which the desired compound is most likely to be capable of effecting its normal biological activity, for example, through receptor or ligand recognition and binding, and comparison of biological activity is made with respect to the compound in association with the micelle or crystalline product of the invention compared to the compound in an aqueous solution or environment. Compounds of the invention may be characterized by having one or more discrete α- or π-helical domains which segregate the hydrophobic and hydrophilic domains. Preferred compounds of the invention are members of the VIP/GRF peptide family. The most preferred compound of the invention is VIP. While biologically active compounds are associated with the micelle core, the association is not irreversible and the compound may be released either quickly or over time from association with the micelle, depending on properties of the micelle and the compound.

In methods of the invention to prepare sterically stabilized crystalline products, any compound that is insoluble in as aqueous solution can be incorporated into to crystalline product. In methods of the invention, the insoluble compounds associate in the hydrophobic core of the associated lipids to the extent that the insoluble compound crystallizes. While the invention contemplates the use of any insoluble compound to produce the crystalline products, preferred compounds are normally insoluble anti-cancer agents, anti-fungal agents, sedatives, and steroidal compounds. Most preferably, the insoluble compounds are selected from the group consisting of Taxol®, betulinic acid, doxorubicin, amphotericin B, diazepam, nystatin, propofol, testosterone, estrogen, prednisolone, prednisone, 2,3 mercaptopropanol, and progesterone.

Micelles according to the invention may be produced from combinations of lipid materials well known and routinely utilized in the art to produce micelles and including at least one lipid component covalently bonded to a water-soluble polymer. Lipids may include relatively rigid varieties, such as sphingomyelin, or fluid types, such as phospholipids having unsaturated acyl chains. The lipid materials may be selected by those of skill in the art in order that the circulation time of the micelles be balanced with the drug release rate. To make full use of the power of these micelles in drug delivery, a key challenge is to prevent the leakage of the drug from the micelle to a level significantly less than the plasma distribution rate. However, this point is probably the fundamental basis of SSL and SSM, since their delivery, which is difficult to control, corresponds to the bioavailability of the encapsulated agent. SSM being more dynamic than liposomes may show superiority to SSL with respect to drug release. Polymers of the invention may thus include any compounds known and routinely utilized in the art of sterically stabilized liposome (SSL) technology and technologies which are useful for increasing circulatory half-life for proteins, including for example polyvinyl alcohol, polylactic acid, polyglycolic acid, polyvinylpyrrolidone, polyacrylamide, polyglycerol, polyaxozlines, or synthetic lipids with polymeric headgroups. The most preferred polymer of the invention is PEG at a molecular weight between 1000 and 5000. Preferred lipids for producing micelles according to the invention include distearoyl-phosphatidylethanolamine covalently bonded to PEG (PEG-DSPE) alone or in further combination with phosphatidylcholine (PC), and phosphatidylglycerol (PG) in further combination with cholesterol (Chol) and/or calmodulin.

Methods of the invention for preparation of sterically stabilized micelle products or sterically stabilized crystalline products can be carried using various techniques. In one aspect, micelle components are mixed in an organic solvent and the solvent is removed using either evaporation or lyophilization. Removal of the organic solvent results in a lipid film, or cake, which is subsequently hydrated using an aqueous solution to permit formation of micelles. The resulting micelles are mixed with an amphipathic compound of the invention whereby the amphipathic compound associates with the micelle and assumes a more favorable biologically active conformation.

In a more simplified preparation technique, one or more lipids are mixed in an aqueous solution after which the lipids spontaneously form micelles. The resulting micelles are mixed with an amphipathic compound which associates with the micelle products and assumes a more favorable biologically active conformation. Preparing micelle products by this method is particularly amenable for large scale and safer preparation and requires a considerable shorter time frame than methods previously described. The procedure is inherently safer in that use of organic solvents is eliminated.

In methods of the invention for preparing sterically stabilized crystalline products, it is preferred that one or more lipid compounds are mixed in an organic solvent with one or more insoluble compounds. The organic solvent is removed either by evaporation or lyophilization to provide a film, or cake. The resulting film, or cake, is then hydrated by introduction of an aqueous solution. As a result, the insoluble compound associates within the hydrophobic core of the lipid structure and is solubilized or re-crystallizes. In one aspect of the invention, the solubilized compound or crystalline product is mixed with a targeting compound which, as described above for preparation of micelle products of the invention, associates with the crystalline product in a more favorable biologically active conformation. Crystalline products of the invention provide advantages in that they, like sterically stabilized micelle products, are able to evade the RES. More importantly, the crystalline products of the invention permit administration of higher concentrations of the insoluble compound in a small volume, preferable in a size less than 300 nm. The crystalline products also provide a method wherein insoluble compounds, which are normally difficult to effectively administer because of their inherent insolubility, can be effectively administered to a mammal in need thereof.

The micelles and crystalline products produced according to the methods of the invention are characterized by improved stability and biological activity and are useful in a variety of therapeutic, diagnostic and/or cosmetic applications. According to one embodiment, the invention comprehends a composition comprising a biologically active micelle product wherein said biologically active amphipathic compound has anti-oxidant activity, anti-aging, anti-wrinkle formation or wound healing capacity. Compositions of this type may be of cosmetic or therapeutic nature. The preferred cosmetic composition includes biologically active VIP. The invention also provides an oral controlled release preparation for the treatment of a gastrointestinal disorder wherein said preparative method further comprises the step of encapsulating the biologically active micelle or crystalline product in an enteric coated capsule. Alternatively, the micelle or crystalline product may be encapsulated in a gelatin capsule. The oral controlled release preparation is useful in a variety of gastrointestinal disorders including those selected from the group consisting of inflammatory bowel disease, chronic constipation, Hirschprung's disease, achalasia, infantile hypertrophic pyloric stenosis, and ulcers. Other indications for use of the micelles of the invention, particularly those micelles containing a member of the VIP/GRF family of proteins, peptides and fragments, analogs, and modulators, include asthma, chronic obstruction pulmonary disease, arthritis, lupus erythematosus, Alzheimer's disease, glaucoma, acute food impaction, scleroderma, rhinitis, systemic and pulmonary hypertension, psoriasis, baldness and impotence. The preferred oral preparation includes biologically active VIP. Micelle preparations comprising biologically active VIP are also a promising therapeutic agent for conditions such as asthma, chronic obstruction pulmonary disease, systemic and pulmonary hypertension, scleroderma, cystic fibrosis, bronchiectasis, myocardial ischemia, impotence and baldness. Still other indications include decreased sperm/ova motility, decreased mucociliary clearance, Kartagener's syndrome, increased inflammatory cell migration and activation, increased secretion of mucin, decreased chloride ion secretion (often associated with cystic fibrosis), vasoconstriction, vascular obstruction to an organ or tissue (often associated with sickle vaso-occlusive crisis), constipation, impotence and female sexual arousal dysfunction. The invention further provides methods for cosmetic use and preserving a bodily organ, tissue, or cell type for storage and transplantation or fertilization in a recipient comprising the step of incubating said organ, tissue, or cell in a micelle composition comprising VIP.

In still another aspect of the invention, micelle products prepared with or without associated amphipathic compounds can be used to improve viability of cells, tissues, and organs that are stored cryogenically. In this aspect, cells are contacted with a micelle product of the invention prior to cryogenic storage either alone, or in the presence of other storage compounds, e.g., dimethylsulfoxide (DMSO), sucrose, glycerol, or ethylene glycol, well known and routinely used in the art.

The invention further provides methods of administering a biologically active amphipathic compound to a target tissue comprising the steps of preparing a biologically active micelle or crystalline product comprising a biologically active amphipathic compound in association with a micelle or crystalline product according to the methods of the invention and administering a therapeutically effective amount of the micelle or crystalline product to said target tissue. The micelle products of the invention may be administered intravenously, intraarterially, intranasally such as by aerosol administration, nebulization, inhalation, or insufflation, intratracheally, intra-articularly, orally, transdermally, subcutaneously, topically onto mucous membranes, such as, but not limited to, oral mucosa, lower gastrointestinal mucosa and conjunctiva, and directly onto target tissues. Methods of administration for amphipathic compounds are equally amenable to administration of compounds that are insoluble in aqueous solutions.

Biologically active compounds in therapeutic methods can be administered at significantly reduced dosage levels as compared to administration of the compound alone, particularly wherein the compound has a particularly short half life or lowered bioactivity in circulation. For example, VIP in association with SSM can be expected to exhibit enhanced and prolonged bioactivity in comparison to VIP administered alone. Regardless of which bioactive compound is associated with SSM, the micelle product must be tested in order to determine a biologically effective amount required to achieve the same result effected by the compound administered by conventional means. The worker of ordinary skill in the art would realize that the biologically effective amount of a particular compound when delivered by conventional means would serve as a starting point in the determination of an effective amount of the compound in SSM. It would therefore be highly predictive that the same and lesser dosages in SSM would be effective as well and merely routine to determine the minimum dosage required to achieve a desired biological effect. In the case of VIP administration, for example, if conventional administration would require a dosage of 20 mg, VIP in SSM would likely require significantly less in order to achieve the same effect. As with administration of amphipathic compounds in association with sterically stabilized micelle products, sterically stabilized crystalline (SSC) products permit administration of more effective dosages of compounds that are insoluble in aqueous solutions.

Association of a biologically active amphipathic or insoluble compound with SSM or SSC product, respectively, of the invention would be expected to increase the magnitude of the biological effects of the compound from about 50 to 100% over the effects observed following administration of the compound alone. Likewise, association with SSM or SSC of the invention would be expected to invoke a longer lasting biological effect.

The invention further provides improved diagnostic compositions comprising biologically active micelle products and methods for their use comprising the steps of: preparing a biologically active micelle product comprising a biologically active amphipathic compound in association with a micelle prepared according to the methods of the invention; administering a diagnostically effective amount of the micelle product to a target tissue or organ; and detecting uptake or interaction of the micelle product at the target tissue or organ. According to one aspect of the invention, the target tissue is a tumor. In one aspect of the method, the micelle product is detectably labeled with a label selected from the group including a radioactive label, a fluorescent label, a non-fluorescent label, a dye, a gas, or a compound which enhances radiographic, magnetic resonance, and ultrasound imaging (MRI) which label is detected at the target tissue.

The invention also provides use of a biologically active micelle product comprising a biologically active amphipathic compound and produced according to methods of the invention for the treatment of inflammation, chronic obstruction pulmonary disease, increased secretion of mucin, acute food impaction, rhinitis, Kartagener's syndrome, cystic fibrosis, bronchiectasis, hypertension, allergy, Alzheimer's disease, atherosclerosis, inflammatory bowel disorder, chronic constipation, Hirschprung's disease, achalasia, infantile hypertrophic pyloric stenosis, ulcers, to enhance or decrease cell proliferation, prevent apoptosis, to promote wound healing in a body organ or tissue, and to prevent cell, organ, and tissue rejection.

Sterically stabilized crystalline products of the invention are particulary useful for administration of anti-cancer agents. For example, crystalline products of the invention comprising Taxol® as the insoluble compound and VIP as the targeting agent can be targeted to breast cancer cells which are known to express higher levels of VIP receptor than normal breast cells, or express receptors with higher affinity of binding for VIP. Taxol® has been shown to selectively kill breast cancer cells.

Cosmetic uses for the micelle and crystalline products of the invention include anti-aging, anti-wrinkling, and anti-oxidant activities, as well as use as a sunscreen.

The present invention is further illustrated by way of the following examples which used the following materials: lipids: L-α-egg yolk phosphatidylcholine type V-E in chloroform: methanol (9:1) (Lot # 34H8395, and 75H8368), L-α-egg yolk phosphatidyl-D-α-Glycerol in chloroform:

methanol (98:2) (Lot # 72H8431, and 85H8395), and cholesterol (Lot #60H0476) from Sigma Chemical Co. (St. Louis, Mo.). Di-Palmitoyl-phosphatidyl choline (Lot #LP-04-01-112-187) from Sygenal Ltd. (Switzerland). PEG-DSPE in lyophilized powder form (Lot # 180PHG2PK-26) from Avanti Polar Lipids Inc. (Alabaster, Ala.). Peptides: VIP (Lot # K02012A1, F02018A1, and K02018A1), VIP fragment 1–12 (Lot # H05009T1), VIP fragment 10–28 (Lot # NB0222), and Vasopressin (Lot # SD1051A) from American Peptide Co. (Sunnyvale, Calif.). Other bio-products: Bovine Brain Calmodulin (Lot # B10537) from Calbiochem Intl. (La Jolla, Calif.). ELISA assay kit (Lot # 976605) from Peninsula Laboratories (Belmont, Calif.). Various chemicals: trehalose (Lot # 43H7060), 2,4-diaminophenol (amidol, Lot # 74H3652), ammonium molybdate (Lot #42H3506), sodium bisulfite (Lot # 41H09432), HEPES (Lot # 43H5720), and sodium chloride (Lot # 22H0724) from Sigma Chemicals Co. (St. Louis, Mo.). Sodium dodecyl sulfate (Lot # 11120KX) from Aldrich Chemical Co., Inc. Perchloric acid 70% (Lot # 945567), chloroform HPLC grade (Lot # 902521) and potassium phosphate monobasic (Lot # 914723) from Fisher Sci. (Pittsburgh, Pa.).

EXAMPLE 1

According to this example, VIP was incorporated into sterically stabilized micelles according to the following procedure. In order to determine the concentration of PEG-DSPE needed to prepare micelles, surface tension studies of PEG-DSPE aqueous solutions were performed. The critical micellar concentration was found to be 0.5 to 1.0 $\mu$M, thus 1.0 $\mu$M of PEG-DSPE was used to ensure formation of micelles (FIG. 1). PEG-DSPE lipid (1 $\mu$mol/ml) was dissolved in chloroform and mixed in a round bottom flask. The organic solvent was evaporated using a rotoevaporater at a bath water temperature of 45° C. (Labconco, Kansas City, Mo.). Complete dryness was achieved by desiccation under vacuum overnight. The dry lipid film was hydrated with saline (0.15 N, pH 6.8) or HEPES buffer (10 mM, pH 7.4). The solution was incubated with human VIP (13 $\mu$g/ml) for 30 min before use in circular dichroism. Human VIP (0.1 nmol/ml) was added to the phospholipid micelle suspension and incubated for 2 hours at room temperature before use in cheek pouch studies.

EXAMPLE 2

According to this example, sterically stabilized micelles comprising VIP and calmodulin were prepared according to the procedure of Example 1 wherein the method of that example was followed to prepare the SSM suspension and during the incubation stage 100 $\mu$l of $10^{-9}$ M CaM was added to 900 $\mu$l of VIP-micelles (giving a total CaM concentration of $10^{-10}$ M) and incubated for 2 h at 4° C. before use in circular dichroism. Human VIP (0.1 nmol/ml) and 100 $\mu$l of $10^{-9}$ M CaM was added to 900 $\mu$l of phospholipid micelles (giving a total CaM concentration of $10^{-10}$ M) and incubated for 2 hours at room temperature before use in cheek pouch studies. VIP concentration of 0.1 nmol was used to allow comparison of results with VIP in sterically stabilized micelle formulation.

EXAMPLE 3

According to this example, the size of the vesicles was determined by quasi elastic light scattering (NICOMP model 270 submicron particle sizer, Pacific Scientific, Menlo Park, Calif.). This device contains a 5 mW Helium-Neon Laser at an excitation wavelength of 623.8 nm and with a 64-channel autocorrelation function, a temperature-controlled scattering cell holder and an ADM 11 video display terminal computer (learr Siegler Inc.) for analyzing the fluctuations in scattered light intensity generated by the diffusion of particles in solution. The mean hydrodynamic particle diameter, $d_h$, was obtained from the Stokes-Einstein relation using the measured diffusion coefficient obtained from analysis of autocorrelation functions accumulated for 30 min. The following instrument settings were used; temperature, 23° C.; viscosity, 0.9325 cp; refractive index, 1.333; and scattering angle, 90°. The sterically stabilized phospholipid micelles (SSM) loaded with vasoactive intestinal peptide (VIP) had a final mean size of ~17.9±0.6 nm.

EXAMPLE 4

According to this example, circular dichroism (CD) experiments were performed to determine the conformation changes of VIP in phospholipid micelles, pH and temperature changes, and in aqueous solutions. CD spectra were recorded on a JASCO J-700 spectropolarimeter using a fused quartz cell of 1 cm pathlength. Spectra in 0.15 N saline (pH 6.8) and 5 mM Hepes buffer (pH 7.4) were measured at a peptide concentration of 4 μM and at a lipid concentration of 1 mM. The effects of CaM, pH (6.8 or 7.4) and temperature (25° C. or 37° C.) on VIP conformation were also studied. The conformation of VIP fragments was likewise studied. All measurements were carried out at room temperature (~25° C.) unless otherwise noted. A bandwidth of 1.0 nm and a step resolution of 0.5 nm were used to collect an average of 9 accumulations/sample at the near-UV range (200–260 nm wavelength). The peptide spectra shown have the background buffer scans, and empty vesicle scans subtracted and were smoothed using the noise reduction function. The temperature during spectral analysis was maintained by using a circulating water bath attached to a jacket surrounding the fused quartz CD cell. The percent helical characterization of VIP was determined by a method of Haghjoo et al., *Peptide Research* 9 (6):327–331 (1996): % helicity=$[-(\theta_{208}+4000)/29000]*100$ and are reported in table 1.

TABLE 1

Percent helical characteristic of the peptide obtained by deconvolution using CD analysis.

| Peptide | % Helicity (in the presence of) | | Molar Ratio |
| --- | --- | --- | --- |
| | Saline | Phospholipids | Peptide: Phospholipid |
| VIP – DPPC*/PG | 2 | 2 | 0.0057 |
| VIP @ Room Temp. | 5 | 27 | 0.0057 |
| VIP @ 37° C. | 2 | 67 | 0.0057 |
| VIP + CaM | 1 | 42 | — |
| CaM | 0 | 0 | 0.0057 |
| VIP$_{1-12}$ | 0 | 0.05 | 0.0057 |
| VIP$_{10-28}$ | 3 | 18 | 0.0057 |
| Vasopressin | 8 | 16 | 0.0057 |

*Di-palmitoyl-phosphatidylcholine

According to the example, CD was used to determine the conformation of VIP in saline, Hepes buffer and phospholipid micelles at room temperature and at 37° C. The CD spectra analysis was performed after 13 μg of human VIP incubated with 1 ml PEG-DSPE (1 μmol) micelles for 30 min at room temperature as determined by preliminary studies. A bandwidth of 1.0 nm and a step resolution of 0.5 nm were used to collect an average of 9 accumulations/sample at near UV range (200–260 nm). The temperature was maintained during spectral analysis by a circulating water bath attached to a jacket surrounding the fused quartz CD cell. The evaluation of VIP molecule conformation in SSM by using circular dichroism was successful because the distortion caused by spherical particles was eliminate due to the small size and univesicular structure of the SSM. The dynamic nature of the micelles also enhanced the VIP interactions with phospholipids. The phospholipid micelles were ideal in our study of VIP conformation since it provided a hydrophobic core similar to the phospholipid bilayer of the SSL. Moreover, both the negative charge, and the hydrophilic layer provided by the PEG mimic the conditions of our SSL and make it possible to infer the VIP conformational results.

The spectral characteristics of VIP in pure water has been shown to be random coil but in organic solvents VIP has been shown to have an α-helix formation (Fournier et al., *Peptides* 5:160–177 (1984); Fry et al., *Biochemistry* 28:2399–2409 (1989); Theriault et al., *Biopolymers* 31:459–464 (1991)). Furthermore, short peptides capable of forming amphipathic helices are known to bind and penetrate lipid bilayers (Noda et al., *Biochim. Biophys. Acta.* 1191:324–330 (1994)). Based on these information VIP is expected to form a helical structure when associated with the micelle.

Figure 2:
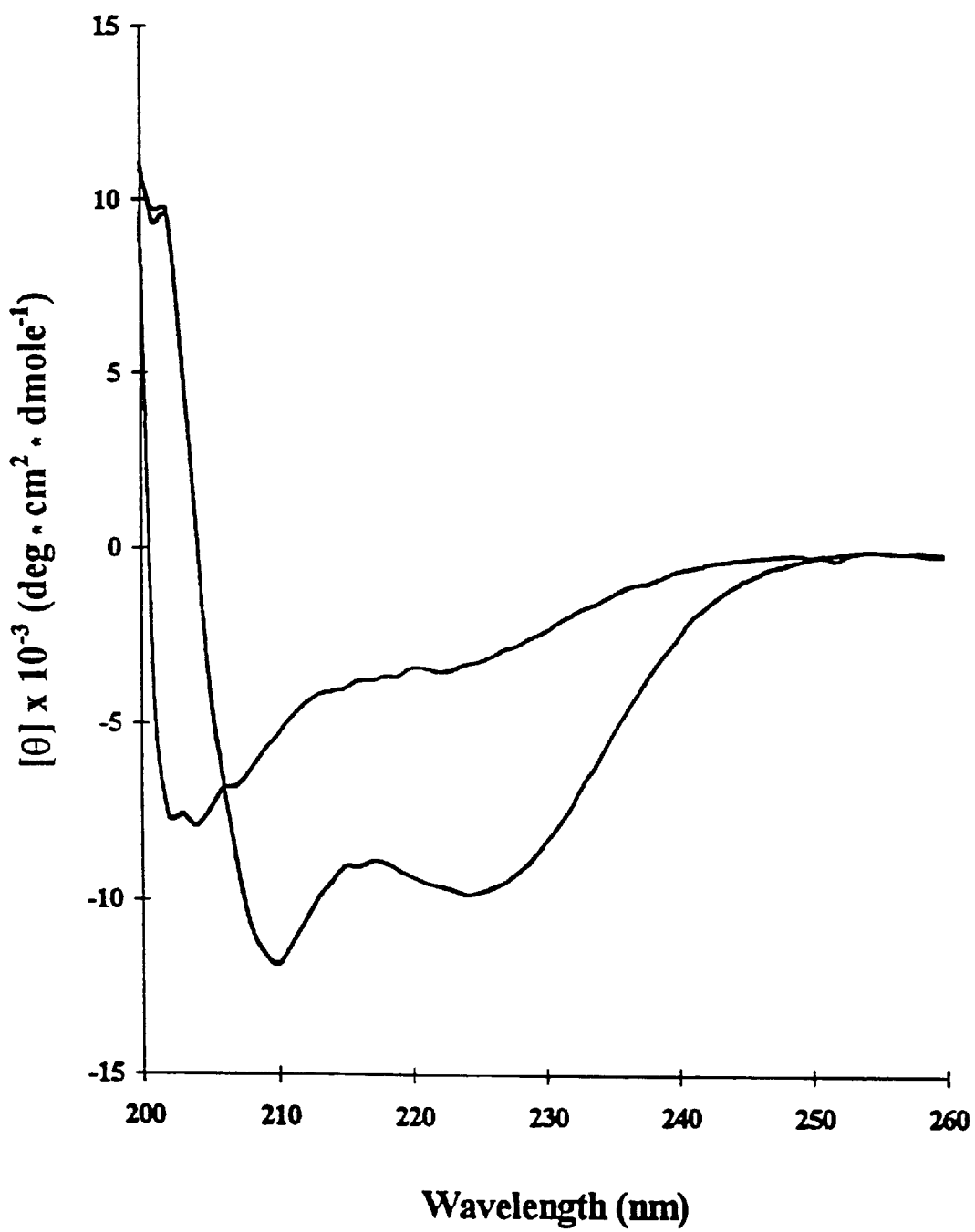
FIG. 2 depicts the CD spectral analysis of VIP in saline, Hepes buffer, and phospholipids at room temperature.

CD spectra of human VIP in saline (pH 6.8) and in the presence of phospholipid micelles are shown in FIG. 2. The studies showed that the peptide has a marked conformational sensitivity to its environment. In the saline, VIP, exhibited a minimum at 203 nm, showing that it is primarily a random coil structure. In the presence of phospholipid micelles, it had a double minimum at 208 nm and 222 nm characteristic of a predominantly α-helix conformation (Table 1).

CD spectra of human VIP in Hepes buffer (pH 7.4) and in the presence of phospholipid micelles are also shown in FIG. 2. (CD spectra analysis of VIP in saline and Hepes buffer (dotted line) compared to VIP in the presence of phospholipids (solid line). Spectrums are average of 9 accumulations/sample.) These studies showed that the peptide in Hepes buffer exhibited a minimum at 203 nm, showing that it is primarily a random coil structure. In the presence of phospholipid micelles, it had a double minimum at 208 nm and 222 nm characteristic of a predominantly α-helix conformation (Table 1). These results are similar to VIP in saline (pH 6.8).

Study of the CD spectra of vasoactive intestinal peptide in saline solution and in the presence of SSM have shown that VIP is in a mostly random coil configuration in saline but in a predominantly α-helix conformation in the presence of SSM. This indicates that VIP, in part, does indeed enter the hydrophobic core despite potential steric hindrance from PEG, and change to its more stable α-helix conformation. Unlike, many amphiphilic molecules the change in the pH showed no significant alterations in VIP conformation suggesting that VIP is not effected by the ionic environment in the range studied.

Figure 3:
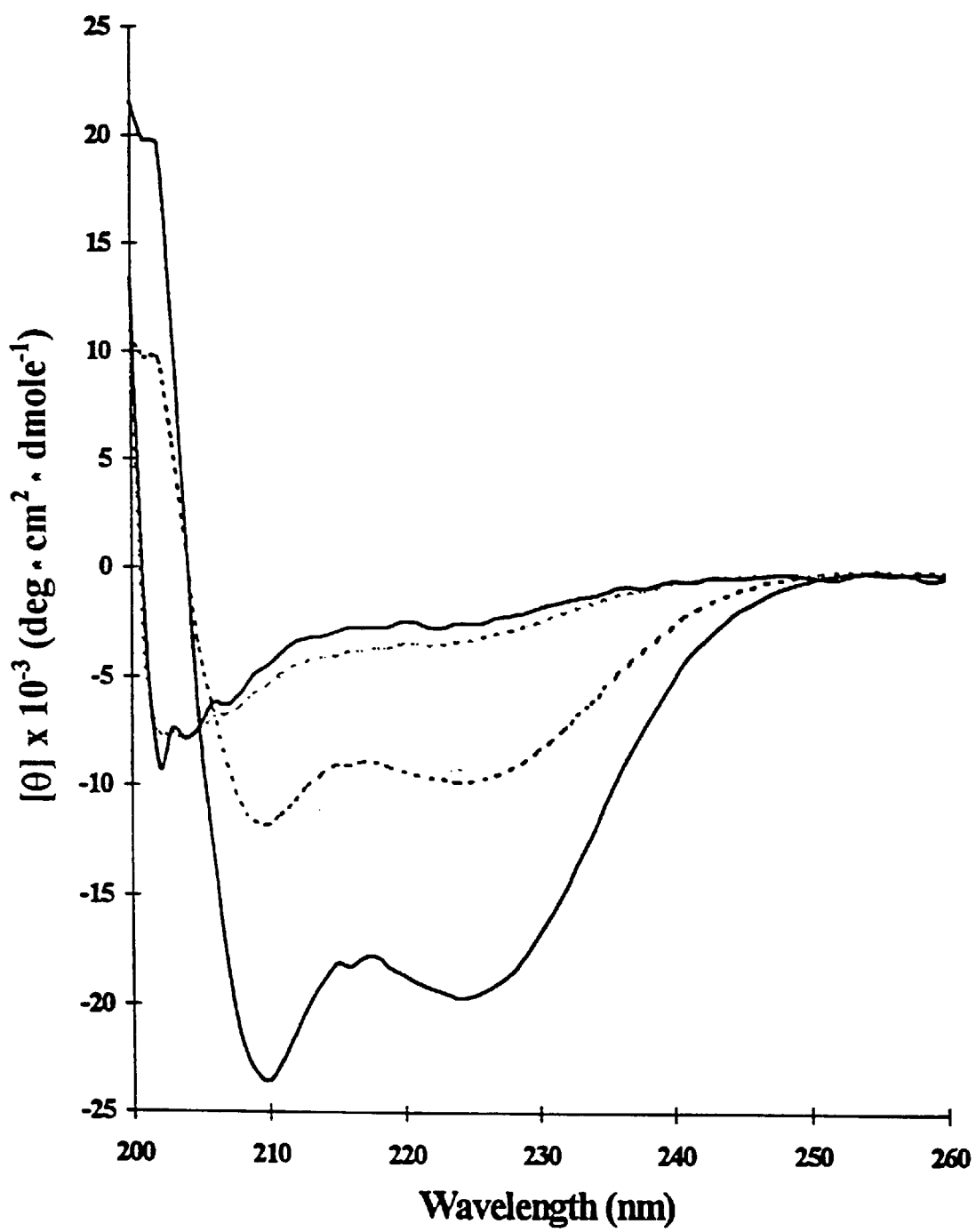
FIG. 3 depicts the CD spectral analysis of VIP at room temperature and at 37°.

CD spectra of human VIP in saline and in the presence of phospholipid micelles at 37° C. are shown in FIG. 3. (CD spectra analysis of VIP in saline at room temperature (dashed line, grey) and at 37° C. (solid line, grey) compared to VIP in the presence of phospholipids at room temperature (dotted line, black) and at 37° C. (solid line, black). Spectrums are average of 9 accumulations/sample.) The studies showed that the absorbance intensity of the peptide in micelles increased at 37° C. compared to room temperature with no change in the spectral shape. The increase in absorbance intensity indicates an amplification of α-helix conformation, as shown by the tripling of the % helical content of VIP (Table 1).

This effect of temperature increase on VIP conformation in SSM is most likely due to the critical micellar temperature (CMT) effects, where CMT is the temperature at which micelles are formed. This increase in the temperature has been shown to be accompanied by an increase in the number of micelles (Nivaggioli et al., *Langmuir.* 11 (3):730–737 (1995)). Increase in the number of micelles leads to an increase in the hydrophobicity of the micellar suspension. Thus, an amplification of α-helix structure of VIP molecules is seen because more of the VIP molecules interact with the micelle or micellar core.

EXAMPLE 5

According to this example, the method of example 4 was repeated to determine the conformation of VIP in saline and phospholipid micelles plus calmodulin (CaM). CD spectra measurements were performed after 13 µg/ml of VIP was incubated with 1.0 µmol/ml of phospholipid micelles for 30 min followed by $10^{-10}$ M CaM incubated with VIP in phospholipid micelles for 2 h at 4° C. (conjugation paper). A bandwidth of 1.0 nm and a step resolution of 0.5 nm were used to collect the average of 9 accumulations/sample at near UV range (200–260 nm).

Figure 4:
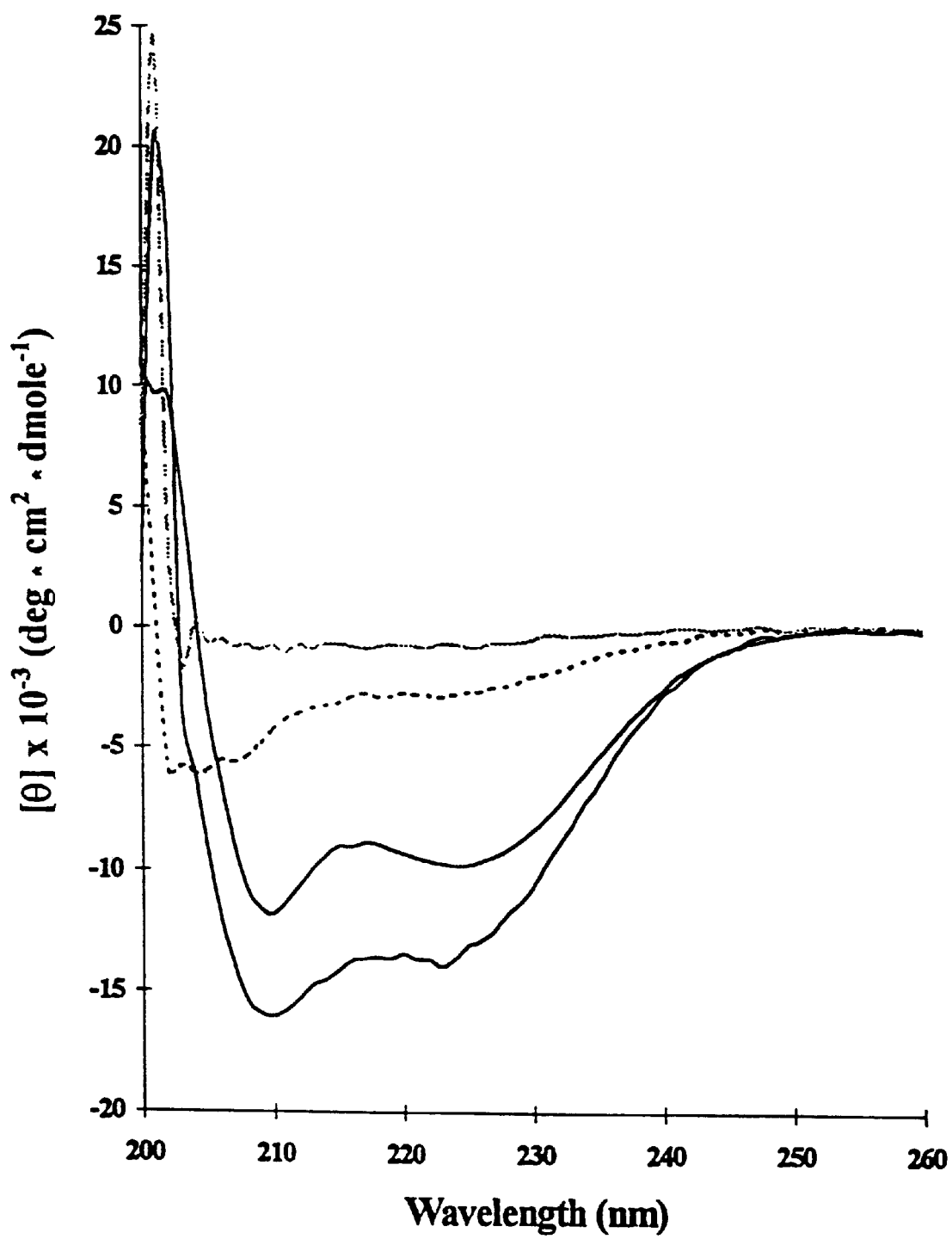
FIG. 4 depicts the effect of calmodulin on the CD spectral analysis of VIP in saline and phospholipids.

CD spectra of human VIP in saline and in the presence of phospholipid in micelles plus CaM are shown in FIG. 4. (CD spectra analysis of VIP+CaM in saline (dotted line, black), CaM in Saline (dotted line, grey) compared to VIP (solid line, grey), and VIP+CaM (solid line, black) in the presence of phospholipids. Spectrums are average of 9 accumulations/sample.) The studies showed that CaM increases the absorbance intensity of VIP in phospholipid micelles without changing the spectral shape. This increase in absorbance indicates an amplification of α-helix conformation, as seen by the doubling of the % helical content of VIP (Table 1). CaM alone had no significant effects on VIP conformation in saline (FIG. 4).

CaM seems to elicit an amplification of the α-helix structure of the VIP in the presence of phospholipids. CaM has been known to interact with phospholipids (Chiba et al., *Life Sciences* 47:953–960 (1990); Houbre et al., *J. Biol. Chem.* 266(11):71217131 (1991); Stallwood et al., *J. Biol. Chem.* 267:19617–19621 (1992); Bolin, *Neurochem. Int.* 23:197–214 (1993); Paul et al., *Neurochem. Int.* 23:197–214 (1993)) and this interaction most likely expose the hydrophobic regions of CaM which induce an increase in the α-helix structure of the VIP. Furthermore, the addition of CaM may decrease the CMC causing the increase in micelle number, which further increases the hydrophobicity of the solution and leads to an amplification of α-helix structure.

EXAMPLE 6

Figure 5:
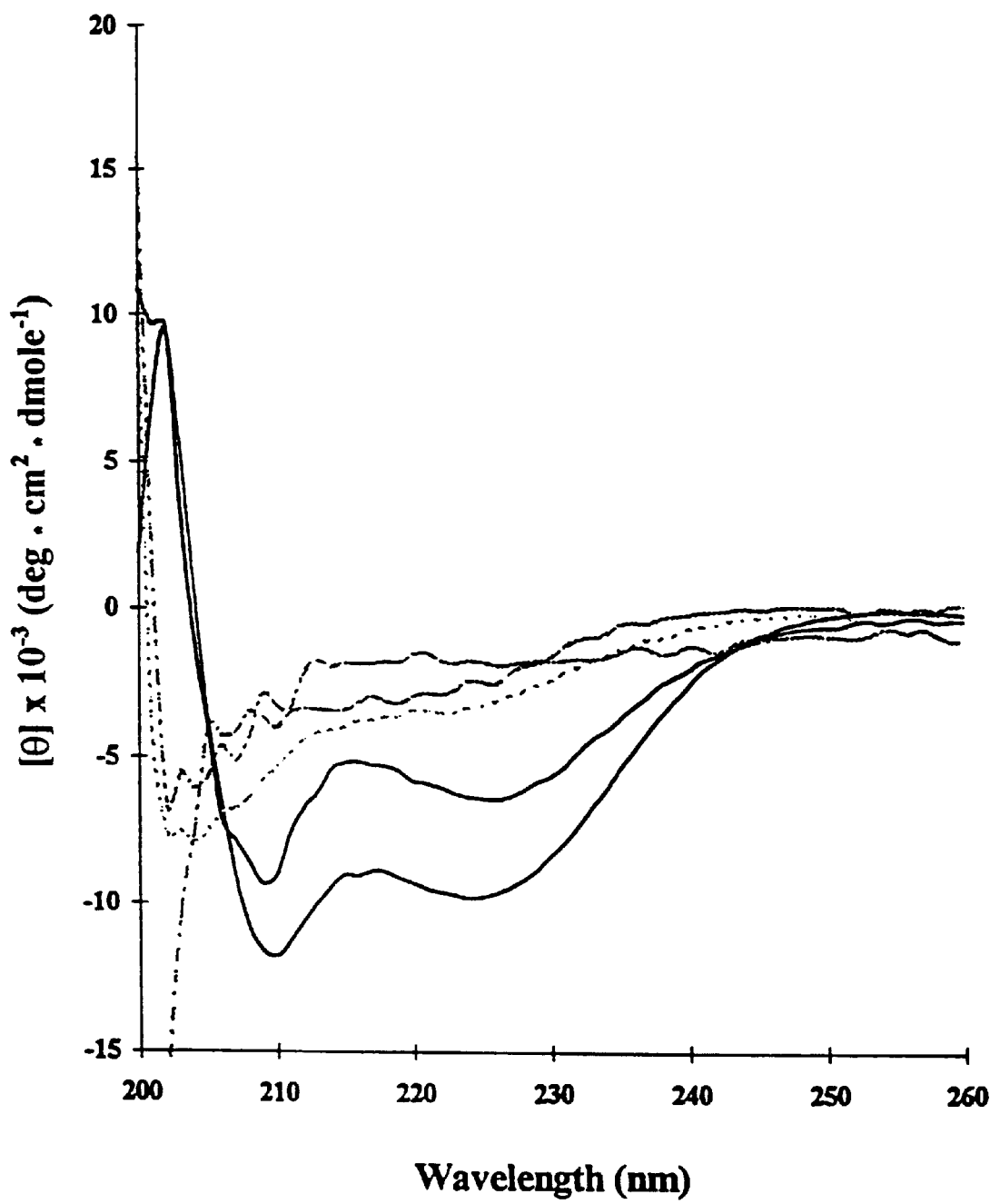
FIG. 5 depicts the CD spectral analysis of VIP fragments in saline and phospholipids.

According to this example the method of example 4 was repeated to determine the conformation of VIP fragments in saline and phospholipid micelles. CD spectra measurements were performed after incubation of VIP fragments with phospholipid micelles, at a molar concentration equivalent to VIP (i.e. 9 µg/ml for $VIP_{10-28}$ fragment and 6 µg/ml for $VIP_{1-12}$ fragment), for 30 min. A bandwidth of 1.0 nm and a step resolution of 0.5 nm were used to collect the average of 9 accumulations/sample at near UV range (200–260 nm). Specifically, CD spectra of human VIP fragment (1–12) and (10–28) in the presence of phospholipid micelles are shown in FIG. 5. (CD spectra analysis of VIP (dashed line, grey), $VIP_{1-12}$ (dash-dot-dot line, grey), and $VIP_{10-28}$ (dashed line, grey) in saline compared to VIP (solid line, black), $VIP_{1-12}$ (dash-dot line, grey), and $VIP_{10-28}$ (solid line, grey), in the presence of phospholipids. Spectrums are average of 9 accumulations/sample.) The spectrum of $VIP_{1-12}$ fragment has a minima at 203 nm in saline and in the presence of SSM indicating a primarily random coil structure. Conversely, the spectrum of $VIP_{10-28}$ in the presence of SSM has a double minima at 208 nm and 225 nm suggesting a predominantly α-helix structure. The spectrum of $VIP_{10-28}$ in saline has a minima at 203 nm indicating a primarily random coil conformation. These effects correlate well with the % helicity of VIP fragments determined in saline and in the presence of phospholipids (Table 1).

The CD spectra of VIP fragments clearly indicate that the α-helix region of the peptide lies in the 10–28 amino acid sequence of the VIP. Others have also observed this phenomenon using CD spectra of VIP in organic solvents. The α-helix formation in $VIP_{10-28}$ aids in explaining its antagonistic bioactivity in vivo. Previously in the inventor's laboratory it was shown that $VIP_{10-28}$ fragment completely abolished native VIP response and attenuated VIP in SSL response in the hamster cheek pouch microcirculation (Séjourné et al., *Pharm. Res.* 14(3):362–365 (1997). This mechanism can be explained by the α-helix structure of $VIP_{10-28}$, which allows the fragment to bind the VIP-receptor site blocking the receptor interaction with VIP. $VIP_{10-28}$ has been reported to bind one type of VIP receptors on smooth muscles (Rorstad et al., *Mol. Pharmacol.* 37:971–977 (1990)).

EXAMPLE 7

The method of example 4 was also repeated to determine the conformation of Vasopressin (VP) in saline and phospholipid micelles at room temperature and at 37° C. CD spectra measurements were performed after incubation of VP with phospholipid micelles, at a molar concentration equivalent to VIP (i.e. 4 µg/ml of VP in 1.0 µmol/ml phospholipids), for 30 min. A bandwidth of 1.0 nm and a step resolution of 0.5 nm were used to collect the average of 9 accumulations/sample at near UV range (200–260 nm). The temperature during spectral analysis was maintained by using a circulating water bath attached to a jacket surrounding the fused quartz CD cell.

Figure 6:
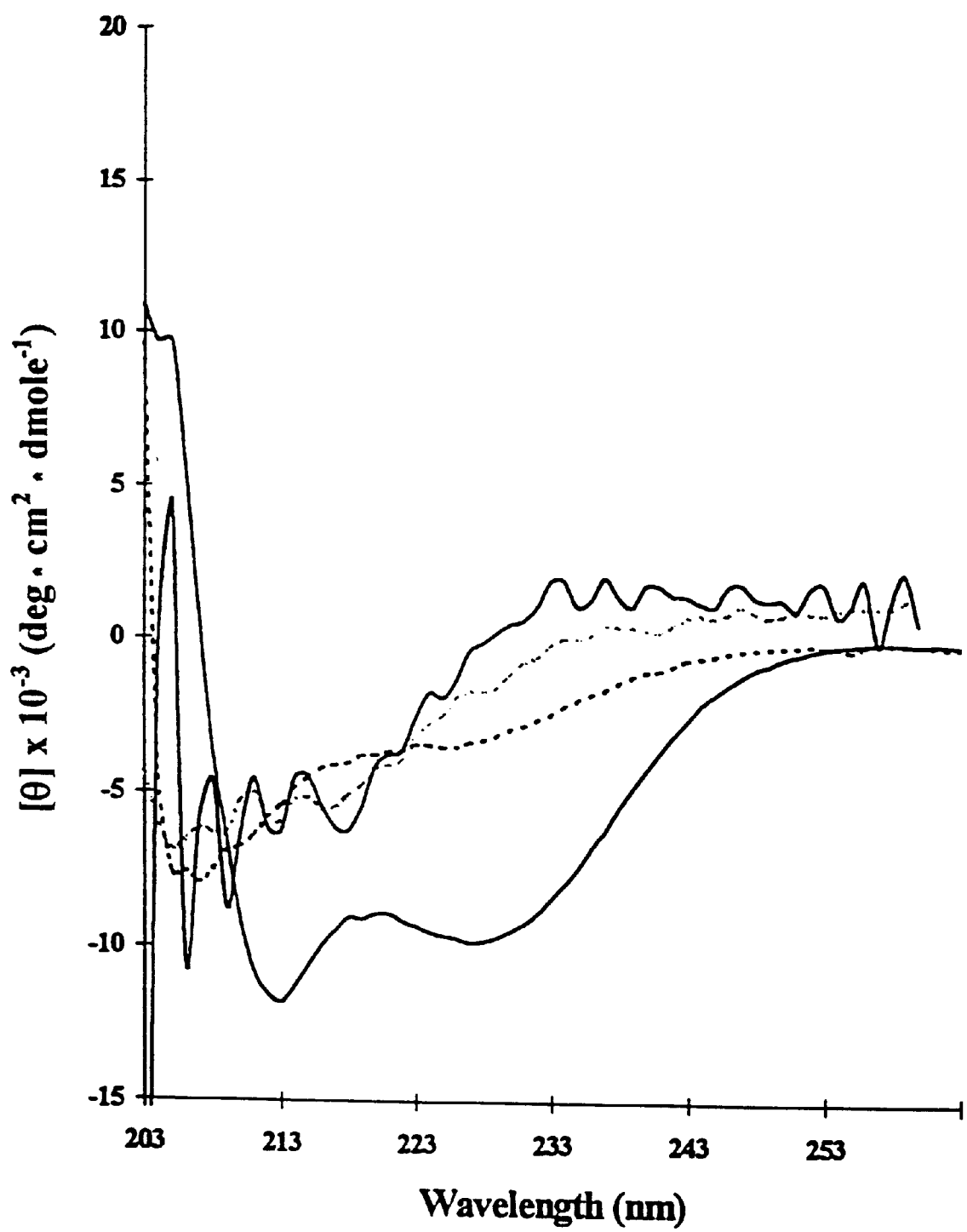
FIG. 6 depicts the CD spectral analysis of VIP and vasopressin (VP) in saline and phospholipids.

Vasopressin (VP) has been tested for long circulation hours and activity after administered as SSL. Therefore, in this study it was attempted to determine if VP also acts by association with the liposomal bilayer. VP was incubated with SSM and CD spectrapolarimetric studies were performed. FIG. 6 (CD spectra analysis of VP (dotted line, grey), and VIP (dotted line, black) in saline compared to VP (solid line, grey), and VIP (solid line, black) in the presence of micelles. Spectrums are an average of 9 accumulations/sample) shows the CD spectra of vasopressin in saline and in the presence of SSM in comparison with VIP spectrums. The spectra indicates that the VP in saline and in the presence of SSM has a similar spectrum with a minima at 204 nm suggesting a primarily random coil conformation, in both cases.

As anticipated vasopressin had no significant changes in its conformation due to the presence of phospholipid micelles, most likely due to its higher affinity to aqueous medium than lipid environment and/or its inflexibility which prevents insertion or penetration into the micellar core.

Therefore, the conformational studies indicate that peptide molecules must be flexible to change its conformation and have an affinity to hydrophobic environment in order to penetrate into the micellar core or lipid bilayer. Furthermore, the negative charge on the PEG-DSPE most likely facilitates the peptide—phospholipid interaction by providing electrostatic attraction. Thus, the CD spectra studies indicate that the VIP most likely enters the hydrophobic micellar core or liposomal bilayer initially due to electrostatic attraction followed by the stable α-helix conformation, which causes the VIP to be in its active conformation for in vivo activity.

EXAMPLE 8

According to this example, the vasorelaxant effects of VIP in a SSM were determined according to the following method. Specifically, adult male golden Syrian hamsters were purchased from Sasco (Omaha, Nebr.). Adult male hamsters with spontaneous hypertension and their normotensive controls were purchased from the Canadian Hybrid Farms (Halls Harbour, NS, Canada). Hypertensive animals have been identified after cross-breeding of hamsters with hereditary cardiomyopathy and normal golden Syrian hamsters. These albino animals have previously been used in our laboratory (Rubinstein et al., *Biochem. Biophys. Res. Commun.* 183:1117–1123 (1992); Artwohl et al., *FASEB J.* 10:A629 (1996)). Animals were anesthetized with pentobarbital sodium (6 mg/100 g body weight, i.p.). A tracheotomy was performed to facilitate spontaneous breathing. A femoral vein was cannulated to inject supplemental anesthesia during the experiment (2–4 mg/100 g body weight/h). Body temperature was maintained constant (37–38° C.) and monitored via heating pad and a feed back controller throughout the experiment.

The bioactivity of the VIP in SSM by diffusing it in situ was determined by visualization of the microcirculation of the hamster cheek pouch. The microcirculation of the cheek pouch was visualized locally by a method previously developed in our laboratory (Suzuki et al., *Life Sci.* 57:1451–1457 (1995); Suzuki et al., *Am. J. Physiol.* 271:R393–R397 (1996); and Suzuki et al., *Am. J. Physiol.* 271:H282–H287 (1996)). Briefly, the left cheek pouch was spread over a small plastic baseplate, and an incision was made in the outer skin to expose the cheek pouch membrane. The connective avascular tissue layer was removed, and a plastic chamber was placed over the baseplate and secured in place by suturing the skin around the upper chamber. This forms a triple-layered complex: the baseplate, the exposed cheek pouch membrane, and the upper chamber. After these initial procedures, the hamster is transferred to a heated microscope stage. The chamber was connected to a reservoir containing warmed bicarbonate buffer (37–38° C.) that allowed continuous suffusion of the cheek pouch. The buffer was bubbled continuously with 95% $N_2$-5% $CO_2$ (pH 7.4). The chamber was also connected via a three way valve to an infusion pump (Sage Instruments, Cambridge, Mass.) that allowed constant administration of drugs into the suffusion buffer.

The cheek pouch microcirculation was epi-illuminated with a 100-W mercury light source and viewed through a microscope (Nikon, Tokyo, Japan) at a magnification of ×40. The image was projected through the microscope and into a closed-circuit television system that consisted of a low-light TV camera, monitor and videotape recorder (Panasonic, Yokohama, Japan). The inner-wall diameter of second order arterioles (44–62 mm), which modulated vascular resistance in the cheek pouch, (Raud, *Acta Physiol. Scand.* (Suppl.) 578:1–58 (1989); Suzuki et al., *Life Sci.* 57:1451–1457 (1995); Suzuki et al., *Am. J. Physiol.* 271:R393–R397 (1996)) was measured from the video display of the microscope image using a videomicrometer (VIA 100; Boeckeler Instruments, Tucson, Ariz.). Magnification calibration of the video system was carried out with a microscope stage micrometer to give microvascular dimensions in micrometers. Clarity on the video monitor screen and location within the arteriolar branching pattern in the cheek pouch were the parameters used to determine the vessels chosen for observation. In some experiments, animals were used in more than one treatment group once measures of arteriolar diameter from previous interventions returned to baseline (see experimental protocols).

Figure 7:
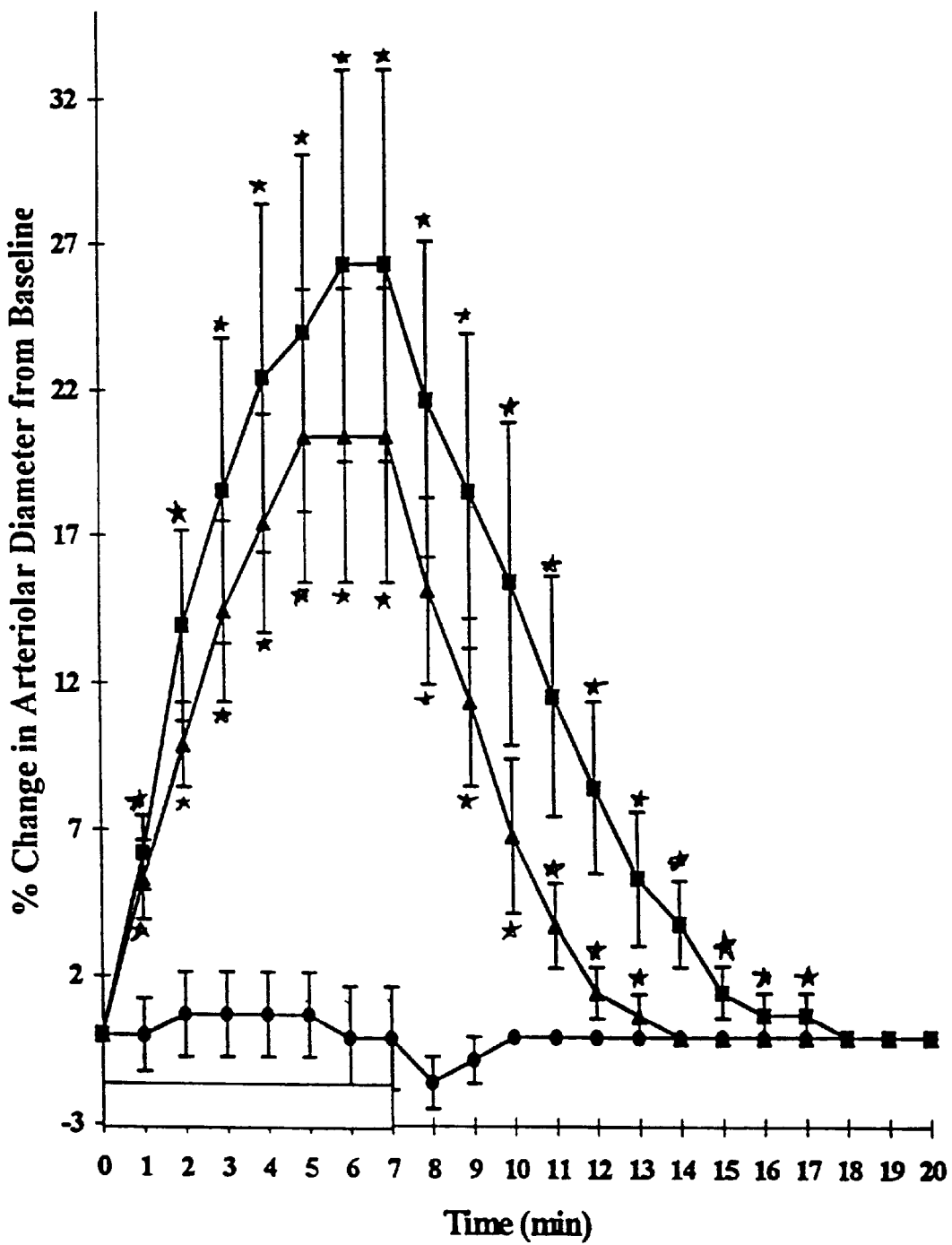
FIG. 7 depicts the effect of VIP-SSM on vasodilation.

Suffusion of 0.1 nmol and 1.0 nmol of VIP in sterically stabilized phospholipid micelles (SSM) for 7 min induced a significant, concentration dependent, and prolonged vasodilation on the arterioles of the hamster cheek pouch microcirculation. There was an increase in arteriolar diameter of 20.2±2.4%, and 24.5±1%, respectively, from baseline values (FIG. 7; mean ±SEM; each group, n=3; p<0.05). Significant vasodilation was observed within 2 min from the start of suffusion and was maximal within 4 min. Arteriolar diameter returned to baseline 7 min (0.1 nmol) and 11 min (1.0 nmol) after VIP-SSM suffusion was stopped. Empty SSM and native VIP alone showed no significant effects on the arteriolar diameter (FIG. 7: Changes in arteriolar diameter during and following suffusion of 0.1 nmol (triangles) and 1.0 nmol (squares) VIP-SSM, and Empty SSM (circles) for 7 min. Open bar, duration of suffusion. Values are mean±SEM; each group, n=4; *p<0.05 compared to baseline.).

The results of the vasorelaxant study showed that the suffusion of VIP in SSM onto the in situ hamster cheek pouch was associated with significant, concentration-dependent and prolonged vasodilation. This prolonged activity of VIP in SSM is surprising since micelles are dynamic and would disintegrate upon suffusion. Thus, the prolonged activity indicates stabilization of the micelles possibly by the presence of VIP that may lead to a formation of VIP—phospholipid complex by hydrophobic interactions, that keeps the micelles intact for a longer period of time. The long lasting activity of VIP-SSM can be attributed to the successful prolonged circulation of the carrier, combined with a stable loading of the peptide, leading to the controlled release of the product. Furthermore, the smaller size of the SSM compared to SSL may additionally increase the circulation time and provide a longer duration of action. In addition, because of the small size of SSM, they are able to migrate into regions inaccessible to liposomes, thereby increasing their biodistribution.

In experiments carried out with the vasoconstrictor peptides angiotensin II and galanin, the same type of increase in biological activity was detected when the peptides were associated with "S1" micelles prepared as described below in Example 11. With angiotensin II at a dose of 0.06 nmol in micelle formulations, vasoconstriction ranged from two to four fold greater than angiotensin II in saline buffer alone. With galanin at a dose of 0.1 nmol in an S1 (Example 11) micelle preparation, vasoconstriction was approximately two times greater than galanin in buffer. At a higher dose (1.0 nmol), the effect of galanin in micelles was still significantly greater (approximately 33%) than galanin in buffer.

EXAMPLE 9

Figure 8:
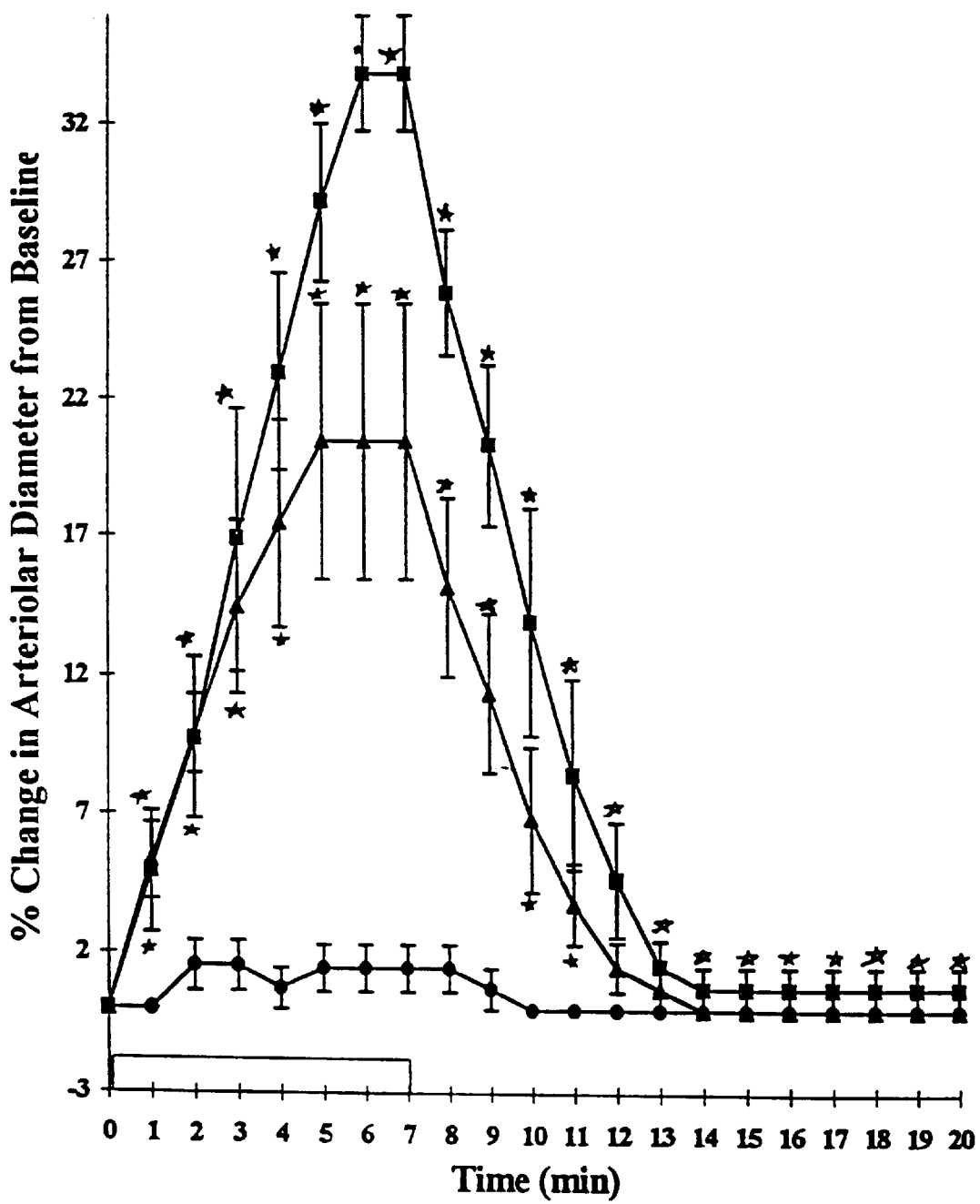
FIG. 8 depicts the effect of calmodulin on VIP-SSM induced vasodilation.

According to this example, the role of calmodulin (CaM) on the vasorelaxant effects of VIP in a SSM were determined according to the methods of example 7. Specifically, a suffusion of 0.1 nmol of VIP+CaM in SSM for 7 min elicited a significant, and prolonged potentiation of VIP-SSM induced vasodilation on the arterioles of the hamster cheek pouch microcirculation. There was an increase in arteriolar diameter of 40±1% from baseline values (FIG. 8; mean ±SEM; each group, n=4; p<0.05). Significant vasodilation was observed within 2 min from the start of suffusion and was maximal within 5 min. Arteriolar diameter returned to baseline 8 min after VIP+CaM-SSM suffusion was stopped. Empty CaM-SSM and native VIP alone showed no significant effects on the arteriolar diameter (FIG. 8: Changes in arteriolar diameter during and following suffusion of 0.1 nmol (triangles) VIP-SSM, 0.1 nmol (squares) VIP+CaM-SSM, and CaM-SSL (circles) for 7 min. CaM concentration was $10^{-10}$ M. Open bar, duration of suffusion. Values are mean ±SEM; each group, n=4; *p<0.05 compared to baseline.)

The results of these studies showed that suffusion of VIP+CaM in SSM potentiated the significant, concentration-dependent, and prolonged vasodilation of the cheek pouch circulation induced by VIP in SSM. These potentiating effects may partly be due to the calmodulin interactions with phospholipid and thus exposing their hydrophobic-protein binding region. Furthermore, this hydrophobic region promotes the α-helix conformation of the VIP due to an increase in the hydrophobic environment of the SSM. The amplification of VIP in the α-helical structure would provide enhanced induction of the receptor-reactive complex and may also increase $2^{nd}$ messenger actions of VIP by promoting direct contact with membranes and membrane-bound proteins. Moreover, the addition of CaM may decrease the CMC causing the increase in micelle number, which further increases the hydrophobicity of the solution and leads to an amplification of α-helix structure. This increase in the amount of active VIP available may be the mechanism by which CaM potentiates the vasodilation of VIP in SSM.

EXAMPLE 10

According to this example, the hypotensive effects of the SSMs of the previous examples on mean arterial pressure are determined.

In order to determine mean arterial pressure a catheter is inserted into the left femoral artery of the hamster to record systemic arterial pressure and heart rate using a pressure transducer and a strip-chart recorder (Model 260, Gould Instrument Systems Inc., Valley View, Ohio.). Continuous anesthesia of the animals limited the monitoring of mean arterial pressure to 6 hours. The cannulated femoral vein was used to administer the products injected intravenously. VIP in SSM (0.1 nmol) is injected intravenous (i.v.) in hypertensive hamsters for 1 min at a rate of 0.5 ml/min. VIP only (0.1 nmol) and empty SSM (concentration equivalent to 0.1 nmol if VIP had been encapsulated, i.e., ~18 nmol phospholipids) are also injected in hypertensive hamsters. The mean arterial pressure (MAP) was calculated every five min for 6 h, and variations associated with the injection of anesthesia were not considered.

According to one aspect of the example the effects of VIP-SSM when administered intravenously in normotensive hamsters is studied. VIP-SSL (0.1 nmol), empty SSL, and VIP only (0.1 nmol) are injected in normotensive hamsters at the same rate as in hypertensive hamsters. The temperature of the hamster is maintained by using a hot water pad placed under the hamster. Intravenous administration of the VIP-SSM in hamsters with spontaneous hypertension is expected to elicit significant and prolonged hypotensive effects.

EXAMPLE 11

According to the present example, an alternative method for producing micelles comprising amphiphilic compounds was designed. This alternative method of preparation, in comparison to the method described in Example 1, is more readily amenable to safe and large scale production of micelles of the invention. The method is exemplified as follows using human galanin, a 30 amino acid neuropeptide with mostly inhibitory, hyperpolarizing biological activity.

DSPE-PEG (16.5 mg, molecular weight 2748.01) was placed in a 20 ml glass vial and 6 ml saline buffer was added to give a final DSPE-PEG concentration of 1.0 μmol/ml. The mixture was vortexed for one minute until the solution was clear, after which the vial was topped with argon and sealed with parafilm. The mixture was allowed to stand at room temperature for one hour or until the bubbles rose out of the mixture. The resulting micelle solution was designated "S1".

Twelve μg human galanin (molecular weight 3158.1) was placed in a polypropylene tube and 5 ml of the S1 micelle preparation was added to the tube giving a final galanin concentration of 1 nmol/1.4 ml. The mixture was vortexed for ten seconds and incubated at room temperature for two hours. The size of the resulting galanin containing micelles, 17 to 20 nm, was measured by QELS as described in Example 3.

EXAMPLE 12

According to the present example, micelle composed of two different compositions were prepared and characterized in order to determine an optimal system for increasing solubility of normally water-insoluble compounds. In the first system, micelles were composed of DSPE-PEG and PC. When DSPE-PEG is mixed with phosphatidylcholine (PC) in aqueous medium, mixed micelles are formed instead of liposome bilayers. In the second system, micelles were formed using PC in combination with a representative bile salt, sodium taurocholate (Sigma). When small molecular weight surfactants, such as bile salts, are mixed with DSPE-PEG, formation of spherical mixed micelles can also be detected. The purpose of this study was (i) to compare the effect of DSPE-PEG and bile salts on phosphatidylcholine (PC) capacity to form mixed micelles; (ii) to examine and compare characteristics of the resulting mixed micelles, including micelle-to-vesicle-transition upon dilution; and (iii) to compare solubilization potential of the two micelle systems.

For both compositions, aqueous detergent-phospholipid mixed micelle stock solutions were prepared by co-precipitation [Alkan-Önyüksel, et al., *Pharm. Res.* 11:206–212 (1994)]. Briefly, egg L-alpha-phosphatidylcholine type XIII-E (Sigma) was combined with either DSPE-PEG 2000 (Avanti) or sodium taurocholate (Sigma) at a PC/detergent molar ration of 0.7 and 0.8, respectively. The mean hydrodynamic diameter of the micelles was measured by quasi-electric light scattering (see Example 3) and small angle neutron scattering (SANS) [Hjelm, et al., *J. Phys. Chem.* 96:8653–8661 (1992)]. In assessing micelle-to-vesicle-transition, the two stock solutions were diluted rapidly in one step and micelle-to-vesicle-transition curves were determined by following the change in aggregate size upon aqueous dilution at room temperature in the presence or absence of counter ions.

The mean size of the DSPE-PC micelles was consistently larger (17 to 22 nm) than micelles containing bile salts (3 to 5 nm). Aqueous dilutions of bile salt mixed micelles resulted in a detectable micelle-to-vesicle-transition, however, no transition was observed under similar conditions with the DSPE-PEG/PC mixed micelles. Bile salts, when added to preformed PC liposome dispersions, resulted in formation of mixed micelles from the pre-existing liposomes, whereas addition of DSPE-PEG to PC liposomes did not demonstrate any vesicle to micelle transition. These results suggest that the hydrophilic PEG component of the DSPE-PEG molecules prevent micelle/micelle or bilayer/micelle interactions. Since DSPE-PEG did not solubilize liposomes, it is anticipated that it will not solubilize a plasma membrane. This result indicated the potential for lower plasma membrane toxicity of DSPE-PEG than bile salts.

Solubilization potential of both micelle compositions for a model drug was measured by HPLC after separation of the unincorporated drug. For purposes of this series of experiments, progesterone, virtually insoluble in an aqueous environment, was chosen as the model drug.

In addition, solubility of progesterone in DSPE-PEG micelles was approximately five to ten times larger than bile salt micelles (from 21 µg/ml to 198±7 µg/ml) for the same total lipid concentration, thereby suggesting that DSPE-PEG micelles have a greater potential as an efficient vehicle for insoluble drugs. However, this dispersion contained both SSM (at approximately 17 nm) and SSC (at approximately 150 nm).

EXAMPLE 13

According to the present example, enhanced solubility of normally water-insoluble compounds was further investigated using a DSPE-PEG micelle composition. In addition, a method for preparing micelles comprising a targeting agent in addition to an encapsulated water-insoluble compound was designed. Drug solubility was determined as follows.

Active drug loading was carried out by adding an excess of drug in powder form to a polyethylene microfuge tube containing PC/bile salt or DSPE-PEG prepared using the film method as previously described in Example 1. Excess drug was removed by centrifugation and the supernatant was analyzed by HPLC. In the case of progesterone, HPLC conditions included a YMC-CN (A-503, 250×4.6 mm inner diameter) column, a mobile phase comprising acetonitrile and water (40:60), and a flow rate of 1.5 ml/minute. HPLC eluent was measured with adsorption at 254 nm. For PC/bile salt mixed micelles, the progesterone to lipid ratio was determined to be 0.0156. For DSPE-PEG micelles, the progesterone to lipid ratio was found to be 0.17.

Results indicated that progesterone (essentially insoluble in water as discussed above) in 10 mg/ml DSPE-PEG was soluble up to 198.5 µg/ml. This result was consistent with results using betullinic acid, sparingly soluble in water (see Merck Index, 12th Edition, p. 1213), which was soluble up to 200 µg/ml in 10 mg/ml DSPE-PEG. In similar experiments with betulinic acid (also insoluble as defined in USP), solubility was calculated at 250 µg/ml in either SSM or SSC.

In design of a targeted drug delivery system comprising micelles, a desired compound is incorporated in micelle compositions as described above. The resulting micelle compositions are then incubated with an amphiphilic compound to allow incorporation of the compound at, and into, the micelle surface as described in Example 1. The membrane associated compound in this arrangement acts as a targeting agent for the entire micelle composition to be delivered to, for example, a receptor for the membrane associated compound. In an alternative approach, the amphilic compound is linked, preferably through covalent modification, to one or the lipid components of the micelle. Through either of these mechanisms, the micelles can carry and deliver the incorporated drug to a target cell or tissue type expressing the cognate receptor.

For example, breast cancer cells express higher levels of VIP receptor than normal breast cells. Micelles comprising membrane associate VIP will therefore preferentially bind to a breast cancer cell rather than a normal cell. Since Taxol® has been shown to kill breast cancer cells, incorporating Taxol® in a VIP/micelle provides a targeted drug delivery for selective killing of the carcinoma cell type.

EXAMPLE 14

According to this aspect of the invention, the effect of infusion of enthelin-1 (ET-1) alone or in a SSM formulation on mean arterial pressure (MAP), cardiac output (CO), total peripheral resistance (TPR), and regional blood circulation in anesthetized rats was examined using a radioactive microsphere technique. SSM with or without ET-1 were prepared according to the method described in Example 11 using DSPE-PEG in saline. Treatments for individual groups consisted of: (i) control, SSM at 2.7 mg/ml (n=6); (ii) ET-1 infusion at 50 ng/kg/min (n=5), and (iii) ET-1 at 50 ng/kg/min in SSM (n=8). Drugs were infused at 0.1 ml/min for 30 minutes.

Results showed that SSM did not affect MAP, CO, TPR or gastrointestinal tract (GIT) blood flow, however, an increase in blood flow to the kidneys (approximately 25%) and brain (approximately 19%) was observed compared to baseline. Blood flow decreased and vascular resistance increased in the kidney, GIT, and brain. ET-1 in SSM produced a significantly marked cardiovascular effect as compared to ET-1 alone. The increase in TPR was 102% in the ET-1 group and 227% in the group treated with ET-1 in SSM. Renal vascular resistance was 76% in the ET-1 group and 281% in the group treated with ET-1 in SSM. However, in brain, vascular resistance was 62% in the ET-1 group and 20% in the group treated with ET-1 in SSM. These results indicated that changes in MAP, TPR and regional vascular resistance are potentiated by ET-1 in SSM.

EXAMPLE 15

According to this aspect of the invention, the ability of micelle products of the invention to enhance cellular viability following cryopreservation was examined. In this experiment, cells were incubated with either DMSO, DSPE-PEG micelle products, or DSPE-PEG micelles products including VIP for 30 minutes prior to storage for 48 hours in liquid nitrogen. Follow removal from the liquid nitrogen, cells were thawed and viability was measured using Trypan blue using standard techniques.

Results indicated that cell viability following treatment with micelles, with or without associated VIP, was equal to or greater than cell viability following treatment with DMSO. Because DMSO is well known and routinely used in the art for cell cryopreservation, these results indicate that micelles can afford equal or better protection, thereby providing an alternative protective agent for cell storage.

Numerous modifications and variations in the invention as set forth in the above illustrative examples are expected to occur to those skilled in the art. Consequently only such limitations as appear in the appended claims should be placed on the invention.

What is claimed is:

1. A method of preparing a biologically active micelle product comprising one or more biologically active amphipathic compounds in association with a micelle; said method comprising the steps of:
   a) mixing one or more lipids wherein at least one lipid component is covalently bonded to a water-soluble polymer;
   b) forming sterically stabilized micelles from lipids;
   c) incubating micelles from step (b) with one or more biologically active amphipathic compound(s) under conditions in which said compound(s) becomes associated with said micelles in a more biologically active conformation.

2. The method according to claim 1 wherein mixing in step (a) is carried out in an organic solvent, and forming sterically stabilized micelles in step (b) is carried out in steps comprising (i) removing the organic solvent to leave a dry film, and (ii) hydrating the dry film with an aqueous solution.

3. The method of claim 2 wherein the organic solvent is removed by evaporation or lyophilization.

4. The method according to claim 1 wherein mixing in step (a) is carried out in an aqueous solution.

5. A method of preparing a biologically active micelle product comprising one or more biologically active amphipathic compounds in association with a micelle; said method comprising the steps of:
   a) mixing one or more lipids with one or more biologically active amphipathic compounds, wherein at least one lipid component is covalently bonded to a water-soluble polymer;
   b) forming sterically stabilized micelles from the mixture of step (a) under conditions in which said compound(s) becomes associated with said micelles in a more biologically active conformation.

6. The method according to claim 5 wherein mixing in step (a) is carried out in an organic solvent and at least one lipid is conjugated to one or more targeting compound(s), and forming micelles in step (b) is carried out in a process comprising the steps of: (i) removing the organic solvent to leave a dry film, and (ii) hydrating the dry film with an aqueous solution, said method further comprising step of: (c) incubating said micelle products under conditions wherein the targeting compound(s) associates with said micelle products in an active conformation.

7. A method for preparing a biologically active sterically stabilized crystalline product comprising one or more biologically active compounds which are insoluble in aqueous solution; said method comprising the steps of:
   a) mixing the biologically active compound(s) with one or more lipids, wherein at least one of the lipids is conjugated to a water soluble polymer; and
   b) forming sterically stabilized crystalline products.

8. The method according to claim 7 wherein mixing in step (a) is carried out in an organic solvent, and forming crystalline products in step (b) is carried out in a process comprising the steps of (i) removing the organic solvent to leave a dry film; and (ii) hydrating the dry film with an aqueous solution, said method further comprising the steps of (c) contacting said crystalline products with one or more targeting compounds; and (d) incubating said crystalline products under conditions wherein the targeting compound(s) associates with said crystalline products.

9. The method according to claim 7 wherein forming in step(b) is carried out in the steps comprising (i) removing the organic solvent to leave a dry film and (ii) hydrating the dry film with an aqueous solution.

10. The method according to any one of claims 1, 5, or 7 wherein said water soluble polymer is polyethylene glycol (PEG).

11. The method according to any one of claims 1, 5 or 7 wherein the amphipathic compound is characterized by having one or more α- or π-helical domains in its biologically active conformation.

12. The method according to claim 11 wherein the compound is a member of the vasoactive intestinal peptide (VIP)/growth hormone releasing factor (GRF) family of peptides.

13. The method according to claim 11 wherein the peptide is selected from the group consisting of VIP, galanin, endothelin, angiotensin II, calmodulin, and fragments, analogs, and modulators thereof.

14. The method according to any one of claims 1, 5, or 7 wherein the micelles have an average diameter of less than about 25 nm.

15. The method of any one of claims 1, 5, or 7 wherein the combination of lipids consists of distearoyl-phosphatidylethanolamine covalently bonded to PEG (PEG-DSPE).

16. A biologically active micelle product produced by the method of any of one claims 1, 5 or 7.

17. A composition comprising the biologically active micelle product of claim 16 wherein said biologically active amphipathic peptide, protein, fragment, analog, or modulators thereof has an activity selected from the group consisting of anti-oxidant activity, anti-pain, anti-inflammatory, wound healing activity, anti-microbial, antibronchospasm, metabolic activity, anti-cancer activity, cardiovascular activity, antiglaucoma activity, anti-apoptosis, anti-wrinkling activity, cryopreservation, and anti-aging activity.

18. The composition according to claim 17 wherein the composition is a cosmetic.

19. The composition according to claim 17 wherein the composition is a therapeutic.

20. A diagnostic composition comprising the micelle composition according to claim 17 and further comprising a detectable label.

21. The diagnostic composition according to claim 20 wherein the label is selected from the group consisting of a fluorescent label, a radioactive label, a dye, a gas, and a compound which enhances radiographic, magnetic resonance, and ultrasound imaging.

22. A diagnostic method comprising the steps of:
   a) preparing a diagnostic composition according to claim 20;
   b) administering a diagnostically effective amount of said composition to a target tissue or organ; and
   c) detecting uptake of the composition at the target tissue or organ by detecting the presence of the label at the target tissue or organ.

23. The method according to claim 22 wherein the label is selected for the group consisting of a fluorescent label, a radioactive label, a dye, a gas, and a compound which enhances radiographic, magnetic resonance, and ultrasound imaging.

24. An oral controlled release preparation for the treatment of a gastrointestinal disorder produced according to the method of claim 12 wherein said method further comprises the step of encapsulating the biologically active micelle product.

25. The oral controlled release preparation of claim 24 wherein the gastrointestinal disorder is selected from the group consisting of inflammatory bowel disease, acute food impaction, chronic constipation, Hirschprung's disease, achalasia, infantile hypertrophic pyloric stenosis, and ulcers.

26. A method of administering a biologically active amphipathic compound to a target tissue or organ comprising the steps of:
   a) a biologically active micelle product comprising a biologically active amphipathic compound in association with a micelle according to the method of any one of claims 1, 5 or 7; and b) administering a therapeutically effective amount of said micelle product to said target tissue or organ.

27. The method according to claim 26 wherein the amphipathic compound in a biologically active conformation is characterized by having one or more α- or π-helical domains.

28. The method of claim 27 wherein said peptide is a member of the vasoactive intestinal peptide (VIP)/growth hormone releasing factor (GRF) family of peptides.

29. The method of claim 27 wherein said peptide is selected from the group consisting of VIP, galanin, endothelin, and angiotensin II and fragments, analogs, and modulators thereof.

30. A method for preserving a bodily organ, tissue or cell type for transplantation or fertilization comprising the step of incubating said organ, tissue, or cell type in the micelle composition produced according to claim 12.

31. The method of claim 7, wherein the soluble compound is selected from the group consisting of progesterone, estrogen, prednisolone, prednisone, 2,3 mercaptopropanol, testosterone, betulinic acid, doxorubicin, amphotericin B, diazepam, nystatin, propofol, and Taxol®.

32. A pharmaceutical composition comprising a crystalline product produced by the method of claim 7.

33. The composition according to claim 32 which is a therapeutic, diagnostic, or cosmetic.

34. A method of administering an insoluble compound to a target tissue comprising the steps of:

a) preparing a biologically active micelle product comprising a biologically active amphipathic compound in association with a micelle prepared according to the method of claim 8; and b) administering a therapeutically effective amount of said micelle product to said target tissue.

* * * * *

UNITED STATES PATENT AND TRADEMARK OFFICE
CERTIFICATE OF CORRECTION

PATENT NO.        : 6,217,886 B1
APPLICATION NO. : 09/239069
DATED             : April 17, 2001
INVENTOR(S)       : Onyuksel et al.

It is certified that error appears in the above-identified patent and that said Letters Patent is hereby corrected as shown below:

In Claim 16, column 32, line 12, please delete "biologically active micelle product" and insert -- biologically active micelle or crystalline product --.

In Claim 17, column 32, line 14, please delete "biologically active micelle product" and insert -- biologically active micelle or crystalline product --.

In Claim 20, column 32, line 29, please delete "micelle."

In Claim 24, column 32, line 55, please delete "biologically active micelle product" and insert -- biologically active micelle or crystalline product --.

In Claim 26, column 32, line 66, please delete "a biologically active micelle product" and insert -- preparing a biologically active micelle or crystalline product --.

In Claim 26, column 33, line 1, please delete "with a micelle according to" and insert -- with a micelle or crystalline product according to --.

In Claim 26, column 33, line 3, please delete "said micelle product" and insert -- said micelle or crystalline product --.

In Claim 34, column 34, line 13, please delete "biologically active micelle product" and insert -- biologically active crystalline product --.

In Claim 34, column 34, line 15, please delete "micelle prepared according to" and insert -- crystalline product prepared according to --.

UNITED STATES PATENT AND TRADEMARK OFFICE
CERTIFICATE OF CORRECTION

PATENT NO.       : 6,217,886 B1
APPLICATION NO. : 09/239069
DATED            : April 17, 2001
INVENTOR(S)      : Onyuksel et al.

It is certified that error appears in the above-identified patent and that said Letters Patent is hereby corrected as shown below:

In Claim 34, column 34, line 17, please delete "said micelle product" and insert -- said crystalline product --.

Signed and Sealed this

Thirtieth Day of January, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,217,886 B1 |
| APPLICATION NO. | : 09/239069 |
| DATED | : April 17, 2001 |
| INVENTOR(S) | : Onyuksel et al. |

Page 1 of 1

It is certified that error appears in the above-identified patent and that said Letters Patent is hereby corrected as shown below:

In the Claims:

In Claim 31, column 34, line 1, please delete "soluble" and insert -- insoluble --.

Signed and Sealed this

Third Day of August, 2010

David J. Kappos
*Director of the United States Patent and Trademark Office*